US009233003B2

(12) United States Patent
Roche et al.

(10) Patent No.: US 9,233,003 B2
(45) Date of Patent: Jan. 12, 2016

(54) REVERSE SHOULDER PROSTHESIS

(75) Inventors: Christopher P. Roche, Gainesville, FL (US); Cary M. Mauldin, Lake City, FL (US); Pierre Flurin, Bordeaux-Merignac (FR); Thomas Wright, Gainesville, FL (US); Joseph Zuckerman, New York, NY (US)

(73) Assignee: Exactech Inc., Gainsville, FL (US)

( * ) Notice: Subject to any disclaimer, the term of this patent is extended or adjusted under 35 U.S.C. 154(b) by 1126 days.

(21) Appl. No.: 11/690,516

(22) Filed: Mar. 23, 2007

(65) Prior Publication Data
US 2007/0244563 A1    Oct. 18, 2007

Related U.S. Application Data

(60) Provisional application No. 60/785,664, filed on Mar. 23, 2006, provisional application No. 60/747,492, filed on May 17, 2006, provisional application No. 60/888,982, filed on Feb. 9, 2007.

(51) Int. Cl.
*A61F 2/40* (2006.01)
*A61B 17/80* (2006.01)
(Continued)

(52) U.S. Cl.
CPC ........... *A61F 2/40* (2013.01); *A61B 17/8047* (2013.01); *A61B 17/86* (2013.01); *A61F 2/4014* (2013.01); *A61F 2/4081* (2013.01); *A61F 2002/2835* (2013.01); *A61F 2002/3056* (2013.01); *A61F 2002/30125* (2013.01); *A61F 2002/30313* (2013.01); *A61F 2002/30538* (2013.01); *A61F 2002/30616* (2013.01); *A61F 2002/30784* (2013.01); *A61F 2002/30901* (2013.01); *A61F 2002/30902* (2013.01); *A61F 2002/4085* (2013.01); *A61F 2230/0008* (2013.01);
(Continued)

(58) Field of Classification Search
CPC .................................. A61F 2/40; A61F 2/4081
USPC ........................................................ 623/19.11
See application file for complete search history.

(56) References Cited

U.S. PATENT DOCUMENTS 3,869,730 A    3/1975  Skobel
3,916,451 A *  11/1975  Buechel et al. .............. 623/23.4
(Continued)

FOREIGN PATENT DOCUMENTS

DE    102006041551 A1 *  11/2007  ................ A61F 2/40
EP    0345133    6/1989
(Continued)

OTHER PUBLICATIONS

"Maior Biojoint System", FINCERAMICA (4 pages).
(Continued)

*Primary Examiner* — Bruce E Snow
*Assistant Examiner* — Melissa Hoban
(74) *Attorney, Agent, or Firm* — Greenburg Traurig, LLP

(57) ABSTRACT

Various embodiments of the present invention relate to an apparatus and method for reverse shoulder arthroplasty (e.g., reverse total shoulder arthroplasty). In one specific example, a glenoid component used to resurface the scapula may be provided. Of note, unlike traditional total shoulder arthroplasty the glenoid component in a reverse shoulder is convex rather than concave; it acts as a physical stop to prevent the superior migration of the humeral head—a typical occurrence in patients suffering from rotator cuff tear arthropathy (CTA).

20 Claims, 62 Drawing Sheets

(51) Int. Cl.
 *A61B 17/86* (2006.01)
 *A61F 2/28* (2006.01)
 *A61F 2/30* (2006.01)

(52) U.S. Cl.
 CPC . *A61F2230/0063* (2013.01); *A61F 2250/0006* (2013.01); *A61F 2250/0074* (2013.01); *A61F 2310/00023* (2013.01); *A61F 2310/00029* (2013.01)

(56) References Cited

U.S. PATENT DOCUMENTS

| | | |
|---|---|---|
| 3,978,528 A | 9/1976 | Crep |
| 4,003,095 A | 1/1977 | Gristina |
| 4,040,131 A | 8/1977 | Gristina |
| 4,179,758 A | 12/1979 | Gristina |
| 4,206,517 A | 6/1980 | Pappas |
| 4,229,840 A | 10/1980 | Gristina |
| 4,261,062 A | 4/1981 | Amstutz et al. |
| 4,279,041 A | 7/1981 | Buchholz |
| 4,328,593 A * | 5/1982 | Sutter et al. ............. 623/23.42 |
| 4,550,450 A | 11/1985 | Kinnett |
| 4,653,487 A | 3/1987 | Maale |
| 4,693,723 A | 9/1987 | Gabard |
| 4,964,865 A | 10/1990 | Burkhead et al. |
| 4,986,833 A | 1/1991 | Worland |
| 5,013,313 A | 5/1991 | Surer |
| 5,032,132 A | 7/1991 | Matsen, III et al. |
| 5,080,673 A | 1/1992 | Burkhead et al. |
| 5,154,719 A | 10/1992 | Cotrel |
| 5,255,838 A | 10/1993 | Gladdish, Jr. et al. |
| 5,314,479 A | 5/1994 | Rockwood et al. |
| 5,437,677 A | 8/1995 | Shearer et al. |
| 5,462,563 A | 10/1995 | Shearer et al. |
| 5,489,310 A | 2/1996 | Mikhail |
| 5,593,448 A | 1/1997 | Dong |
| 5,611,800 A | 3/1997 | Davis et al. |
| 5,702,447 A | 12/1997 | Walch et al. |
| 5,702,453 A | 12/1997 | Rabbe et al. |
| 5,800,551 A | 9/1998 | Williamson et al. |
| 5,976,141 A | 11/1999 | Haag et al. |
| 5,989,254 A | 11/1999 | Katz |
| 6,045,582 A | 4/2000 | Prybyla |
| 6,156,069 A | 12/2000 | Amstutz |
| 6,228,119 B1 | 5/2001 | Ondrla et al. |
| 6,228,120 B1 | 5/2001 | Leonard |
| 6,364,910 B1 | 4/2002 | Shultz et al. |
| 6,379,386 B1 | 4/2002 | Resch et al. |
| 6,406,495 B1 | 6/2002 | Schoch |
| 6,514,287 B2 | 2/2003 | Ondrla et al. |
| 6,673,115 B2 | 1/2004 | Resch et al. |
| 6,679,916 B1 | 1/2004 | Frankle et al. |
| 6,699,289 B2 | 3/2004 | Iannotti et al. |
| 6,736,851 B2 | 5/2004 | Maroney |
| 6,790,234 B1 | 9/2004 | Frankle |
| 6,911,047 B2 | 6/2005 | Rockwood, Jr. et al. |
| 7,241,314 B1 | 7/2007 | Winslow |
| 7,462,197 B2 | 12/2008 | Tornier et al. |
| 7,621,961 B2 | 11/2009 | Stone |
| 7,753,959 B2 | 7/2010 | Berelsman et al. |
| 2003/0158605 A1 | 8/2003 | Tornier |
| 2004/0006342 A1 | 1/2004 | Altarac et al. |
| 2004/0034433 A1 | 2/2004 | Chan et al. |
| 2004/0059424 A1 | 3/2004 | Guederian et al. |
| 2004/0064190 A1 | 4/2004 | Ball et al. |
| 2004/0122519 A1 | 6/2004 | Wiley et al. |
| 2004/0122520 A1 | 6/2004 | Lipman et al. |
| 2004/0138754 A1 | 7/2004 | Lang et al. |
| 2004/0220673 A1 | 11/2004 | Pria |
| 2004/0225360 A1 | 11/2004 | Malone |
| 2004/0225367 A1 | 11/2004 | Glien et al. |
| 2004/0236424 A1 | 11/2004 | Berez et al. |
| 2005/0015131 A1 | 1/2005 | Fourcault et al. |
| 2005/0049709 A1 | 3/2005 | Tornier |
| 2005/0060039 A1 | 3/2005 | Cyprien |
| 2005/0209700 A1 | 9/2005 | Rockwood et al. |
| 2005/0261775 A1 | 11/2005 | Baum et al. |
| 2005/0278032 A1 | 12/2005 | Tornier et al. |
| 2006/0020344 A1 | 1/2006 | Shultz et al. |
| 2006/0229726 A1 | 10/2006 | Ek |
| 2006/0235537 A1 | 10/2006 | Kuczynski et al. |
| 2006/0259148 A1 | 11/2006 | Bar-Ziv |
| 2008/0058949 A1 | 3/2008 | Dees et al. |
| 2009/0149961 A1 * | 6/2009 | Dallmann ................. 623/19.11 |

FOREIGN PATENT DOCUMENTS

| | | | |
|---|---|---|---|
| EP | 0 538 895 | 4/1993 | |
| EP | 0845250 A2 * | 6/1996 | ............... A61F 2/36 |
| EP | 0 998 885 | 5/2000 | |
| EP | 1 064 890 A1 | 1/2001 | |
| EP | 1 486 183 | 12/2004 | |
| EP | 1486 183 | 12/2004 | |
| EP | 152 0561 | 4/2005 | |
| FR | 2652498 | 4/1991 | |
| FR | 2776506 | 10/1999 | |
| FR | 279 0 198 | 1/2000 | |
| FR | 2 871 369 A1 | 12/2005 | |
| GB | 2405346 | 3/2005 | |
| WO | 2004/080331 | 9/2004 | |

OTHER PUBLICATIONS

Boileau, P. et al. Grammont Reverse Prosthesis: Design, Rationale, and Biomechanics. JSES Jan./Feb. 147S-161S. 2005.
Checroun, A. J. et al. Fit of Current Glenoid Component Designs: an Anatomic Cadaver Study. JSES. vol. 11, #6: 614-617. 2002.
De Wilde, L. et al. Shoulder Prosthesis Treating Cuff Tear Arthropathy: a comparative biomechanical study. JOR 22: 1222-1230. 2004.
De Wilde, L. et al. Functional Recovery after a Reverse Prosthesis for Reconstruction of the Proximal Humerus in Tumor Surgery. CORR. #430: 156-162. 2005.
Grammont, P. M. et al. Etude et Realisation D'une Novelle Prosthese D'Paule. Rhumatologie. #39: 17-22. 1987.
Iannotti, J. P. et al. The Normal Glenohumeral Relationships. JBJS. vol. 74-A, #4: 491-500 1992.
Katzer, A. Two-Year Results After Exchange Shoulder Arthroplasty Using Inverse Implants. Orthopedics. vol. 27, #11: 1165-1167. 2004.
Mell, A. G. et al. Effect of Rotator Cuff Tear Size on Shoulder Kinematics. Transactions of the 51st Annual Meeting of the Orthopaedic Research Society. Poster #0623. 2005.
Neer, C. S. et al. Cuff Tear Arthropathy. JBJS. #65: 1232-1244. 1983.
Nyffeler, R.W. et al. Biomechanical Relevance of Glenoid Component Positioning in the Reverse Delta III Total Shoulder Prosthesis. JSES. vol. 14 # 5: 524-528. Sep./Oct. 2005.
Rittmeister, M. et al. Grammont Reverse Total Shoulder Arthroplasty in Patients with Rheumatoid Arthritis and Nonreconstructable Rotator Cuff Lesions. JSES. Jan./Feb.: 17-22. 2001.
Sirveaux, F. et al. Grammont inverted total shoulder arthroplasty in the treatment of glenohumeral osteoaitis with massive rupture of the cuff. JBJS 86-B: 388-395. 2004.
Vanhove, B. Grammont's Reverse Shoulder Prosthesis for Rotator Cuff Arthropathy. A Retrospective Study of 32 Cases. Acta Orthop Belg. #70 (3): 219-225. 2004.
Supplementary European Search Report issued in European Patent Appln. No. 07759285.5 dated Mar. 19, 2012.
Boileau et al., "Neer Award 2005: The Grammont reverse shoulder prosthesis: Results in cuff tear arthritis, fracture sequelae, and revision arthroplasty", J Shoulder Elbow Surg Sep./Oct. 2006; © 2006 Journal of Shoulder and Elbow Surgery Board of Trustees, pp. 527-240.
Boileau et al., "Grammont reverse prosthesis: Design, rationale, and biomechanics", J Shoulder Elbow Surg Jan./Feb. 2005; © 2005 Journal of Shoulder and Elbow Surgery Board of Trustees, pp. 147S-161S.
Boileau et al., "Normal and pathological Anatomy of the glenoid", in Shoulder Arthroplasty; Springer-Verlag Heidelberg, pp. 127-140, 1990 <<http://www.maitrise-orthop.com/viewPage.do?id=575>>.

(56) References Cited

OTHER PUBLICATIONS

Bufquin et al., "Reverse shoulder arthroplasty for the treatment of three- and four-part fractures of the proximal humerus in the elderly—A Prospective Review of 43 Cases with a Short-Term Follow-up" The Journal of Bone & Joint Surgery (Br) 2007; pp. 516-520.

Farron et al., "Risks of loosening of a prosthetic glenoid implanted in retroversion", J Shoulder Elbow Surg Jul./Aug. 2006, © 2006 Journal of Shoulder and Elbow Surgery Board of Trustees, pp. 521-526.

Gillespie et al., "Eccentric Reaming in Total Shoulder Arhtroplasty: A Cadaveric Study", Orthopedics 2009; pp. 1-7<<http://www.orthosupersite.com/view.asp?rid=33723>>.

Hopkins et al., "The effects of glenoid component alignment variations on cement mantle stresses in total shoulder arthoplasty", J Shoulder Elbow Surg, vol. 13, No. 6, © 2004 Journal of Shoulder and Elbow Surgery Board of Trustees, pp. 668-675.

Nuttall et al., "A study of the micromovement of pegged and keeled glenoid components compared using radiostereometric analysis", J Shoulder Elbow May/Jun. 2007, vol. 16, No. 3S; © 2007 Journal of Shoulder and Elbow Surgery Board of Trustees, pp. 65S-70S.

Shapiro et al. "Biomechanical effects of glenoid retroversion in total shoulder arthroplasty", J Shoulder Elbow May/Jun. 2007, vol. 16, No. 3S; © 2007 Journal of Shoulder and Elbow Surgery Board of Trustees, pp. 90S-95S.

Simovitch et al., "Predictors of Scapular Notching in Patients Managed with the Delta III Reverse Total Shoulder Replacement", The Journal of Bone & Joint Surgery 2007; 89, pp. 588-600.

Sirveaux et al., Grammont inverted total shoulder arthroplasty in the treatment of glenohumeral osteoarthritis with massive rupture of the cuff—Results of a Multicentre Study of 80 Shoulders; The Journal of Bone & Joint Surgery (Br); 2004; 86-B, pp. 388-395.

Stechel et al., "Reversed shoulder arthroplasty in cuff tear arthritis, fracture sequelae, and revision arthroplasty", Acta Orthopaedica 2010; 81 (3), pp. 367-372.

Vanhove et al., "Grammont's reverse shoulder prosthesis for rotator cuff arthropathy. A retrospective study of 32 cases", Acta Orthop. Belg., 2004, 70, pp. 219-225.

Werner et al., "Treatment of Painful Pseudoparesis Due to Irreparable Rotator Cuff Dysfunction with the Delta III Reverse-Ball-and-Socket Total Shoulder Prosthesis", The Journal of Bone & Joint Surgery, vol. 87-A, No. 7, Jul. 2005, pp. 1476-1486.

Yian et al., "Radiographic and Computer Tomography Analysis of Cemented Pegged Polyethylene Glenoid Components in Total Shoulder Replacement", The Journal of Bone & Joint Surgery, vol. 87-A, No. 9, Sep. 2005, pp. 1928-1936.

* cited by examiner

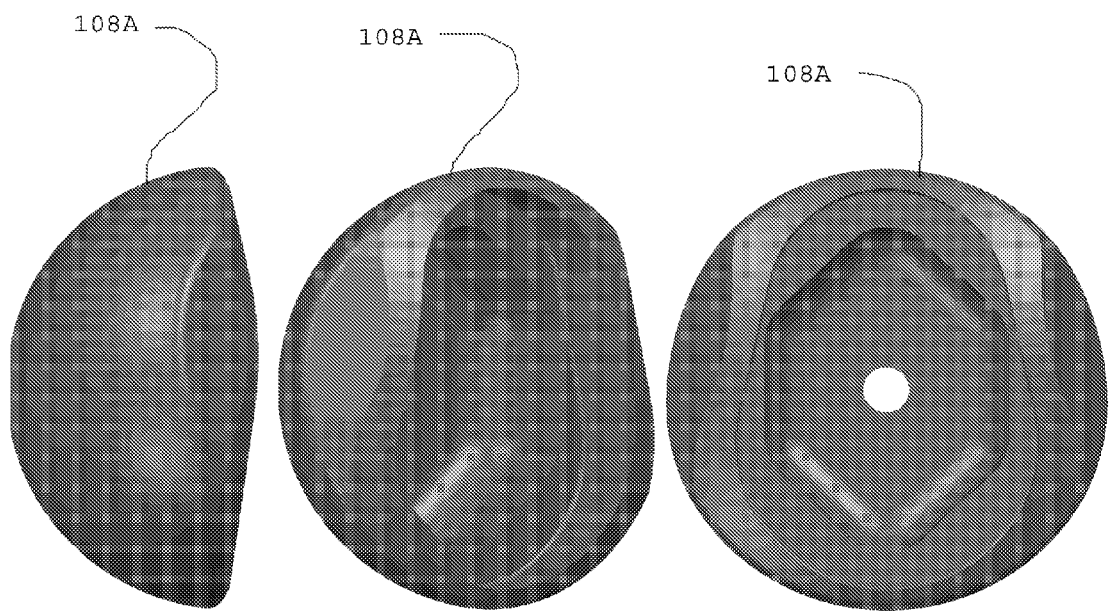

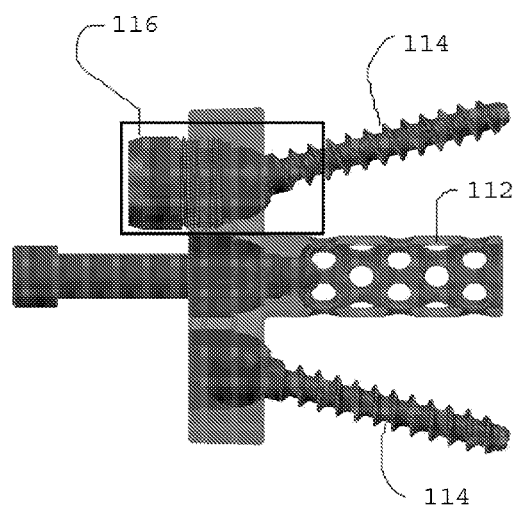
Fig. 9A
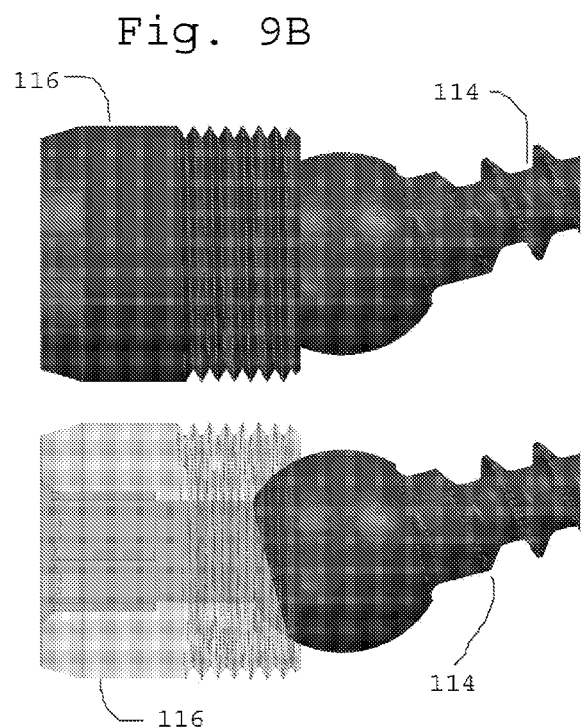
Fig. 9B
Fig. 9C

29mm Glenosphere Plate (Approximate Diameter and Hole Position of the Grammont and Encore Design)

| Humeral Neck Angle | 130° | 135° | 140° | 145° | 150° | 155° | 160° | 165° |
|---|---|---|---|---|---|---|---|---|
| Inferior Impingement | 10° | 15° | 20° | 25° | 30° | 35° | 40° | 45° |
| Superior Impingement | 70° | 75° | 80° | 85° | 90° | 95° | 100° | 105° |
| ROM | 60° | 60° | 60° | 60° | 60° | 60° | 60° | 60° |

Fig. 40

| Humeral Constraint | 0.2500 | 0.2625 | 0.2750 | 0.2875 | 0.3000 | 0.3125 |
|---|---|---|---|---|---|---|
| Inferior Impingement | 31.5° | 33° | 35° | 37° | 38.5° | 40.5° |
| Superior Impingement | 99° | 97° | 95° | 93° | 91.5° | 89.5° |
| ROM | 67.5° | 64° | 60° | 56° | 53° | 49° |

Fig. 41

| Glenosphere Thickness* | 17mm | 18mm | 19mm | 20mm | 21mm |
|---|---|---|---|---|---|
| Inferior Impingement | 40.5° | 38° | 35° | 32° | 29.5° |
| Superior Impingement | 89.5° | 92° | 95° | 98° | 100.5° |
| ROM | 49° | 54° | 60° | 66° | 71° |

*Assumes a constant humeral liner constraint between sizes

Fig. 42

| Glenosphere Diameter* | 34mm | 36mm | 38mm | 40mm | 42mm | 44mm |
|---|---|---|---|---|---|---|
| Impingement at 0° ABD | 11.3mm | 11.9mm | 12.4mm | 12.9mm | 13.5mm | 14.0mm |
| Jump Distance at 35° ABD | 18.0mm | 19.0mm | 20.0mm | 20.9mm | 21.9mm | 22.9mm |
| Jump Distance at 65° ABD | 7.9mm | 8.4mm | 8.8mm | 9.3mm | 9.8mm | 10.2mm |
| Jump Distance at 90° ABD | 2.0mm | 2.1mm | 2.2mm | 2.3mm | 2.4mm | 2.5mm |
| *Assumes a constant humeral liner constraint between sizes | | | | | | |

Fig. 43

| | 38mm Equinoxe | 42mm Equinoxe | 46mm Equinoxe | 36mm Grammont | 42mm Grammont* |
|---|---|---|---|---|---|
| Inferior Impingement | 16° | 7.5° | 0° | 35° | 35° |
| Superior Impingement | 91.5° | 91.5° | 91.5° | 95° | 95° |
| ROM | 75.5° | 84° | 91.5° | 60° | 60° |

*Assumes 42mm Grammont has the same humeral liner constraint as the 36mm Grammont

Fig. 58

REVERSE SHOULDER PROSTHESIS

RELATED APPLICATIONS

This application claims the benefit of U.S. Provisional Application Ser. No. 60/785,664, filed Mar. 23, 2006. This application also claims the benefit of U.S. Provisional Application Ser. No. 60/747,492, filed May 17, 2006. This application also claims the benefit of U.S. Provisional Application Ser. No. 60/888,982, filed Feb. 9, 2007. Each of the aforementioned applications is incorporated herein by reference in its entirety.

FIELD OF THE INVENTION

Various embodiments of the present invention relate to an apparatus and method for reverse shoulder arthroplasty (e.g., reverse total shoulder arthroplasty). In one specific example, a glenoid component used to resurface the scapula may be provided. Of note, unlike traditional total shoulder arthroplasty the glenoid component in a reverse shoulder is convex rather than concave; it acts as a physical stop to prevent the superior migration of the humeral head—a typical occurrence in patients suffering from rotator cuff tear arthropathy (CTA).

For the purposes of describing the present invention the term "Equinoxe" (such as, for example, Equinoxe reverse shoulder design or Equinoxe reverse shoulder prosthesis) is intended to refer to an embodiment of the present invention.

BACKGROUND OF THE INVENTION

Neer coined the term cuff tear arthropathy in 1972 to describe the arthritic, eroded/collapsed condition of the glenohumeral joint following prolonged/progressive subacromial impingement resulting from massive, full thickness rotator cuff tears. This pathology is associated with extreme pain and near complete loss of function. (see Neer, C. S. et al. Cuff Tear Arthropathy. JBJS. #65: 1232-1244. 1983).

Cuff tear arthropathy has been historically treated with acromioplasty, arthroscopic debridement, tendon transfers, humeral tuberoplasty, arthrodesis, total shoulder arthroplasty (constrained, semi-constrained, or unconstrained), bipolar shoulder arthroplasty, hemiarthroplasty (with and without acromial spacers), and most recently (and successfully) reverse shoulder arthroplasty.

The Reverse/Inverse shoulder was first conceived by Neer in the early 1970's to treat patients suffering from CTA; specifically, this device was intended to provide pain relief and prevent progressive acromial, coracoid, and glenoid erosion by resisting humeral head superior migration. This was theoretically accomplished by inverting the male and female ball and socket so that the glenoid component was now convex and the humerus now concave; doing so created a physical stop that prevents the humerus from migrating superiorly. Several reverse shoulder designs have since been conceived and developed: the Fenlin, Reeves, Gerard, Kessel, Kolbel, and the Neer-Averill to name but a few; of these, only the Kessel design has reported long-term outcomes (it is believed that each of the aforementioned designs have since been abandoned). Similar to constrained total shoulder arthroplasty, the fixed center of rotation resulted in an excessive torque on the glenoid that compromised fixation, ultimately leading to loosening.

In 1987, Paul Grammont introduced a new reverse shoulder design. It consisted of 2 components: the glenoid was a metallic or ceramic 42 mm ball (~⅔ of a sphere) and the humeral component was a polyethylene "trumpet-shaped" cup (whose concave surface was ~⅓ of a sphere); the humeral component was fixed with PMMA. The preliminary results of this prosthesis were published in 1987 (see Grammont, P. M. et al. Etude et Realisation D'une Novelle Prosthese D'Paule. Rhumatologie. #39: 17-22. 1987); after a mean follow-up of six months, all six patients (8 shoulders) were pain-free; however, mobility was variable: 3 patients had active anterior elevation between 100-130°, 3 patients had active anterior elevation less than 60°. These inconsistent results necessitated a redesign.

In 1991, the Grammont reverse shoulder was redesigned and renamed as the Delta III reverse shoulder prosthesis. The cemented glenoid failed; therefore, the glenosphere was redesigned to have a fixed central peg and divergent screws. The ⅔ of a sphere in the glenoid was abandoned for ⅓ of sphere to place center of rotation directly in contact with glenoid fossa; thereby, reducing the torque on the bone surface. The humeral component was designed for either cemented or uncemented applications (see Boileau, P. et al. Grammont Reverse Prosthesis: Design, Rationale, and Biomechanics. JSES January/February: 147S-161S. 2005).

This prosthesis was called the "Delta" because of its functional dependence on the Deltoid. The design rationale for the Delta III is described as follows:
- the center of rotation is shifted medially (to increase the effective lever arm of the deltoid by recruiting more of the deltoid fibers for elevation and abduction).
- the center of rotation is shifted distally by lowering the humerus (to tension the deltoid).
- the center of the glenosphere is placed directly on the glenoid fossa to limit the torque on the fixation devices and resist loosening.
- the inverted concavities of the glenohumeral joint create a physical stop to prevent humeral head superior migration; the status of the CA arch is irrelevant with this design.

Whether these theoretical biomechanical benefits of the Delta will actually become realized has yet to be determined as there has been limited long-term outcome studies (>5 yrs) which demonstrate its reliability; however, short-term and medium-term outcome studies suggest that the design provides pain relief and restores function (primarily in abduction/adduction and partially in flexion/extension; internal/external rotation is restored on a limited basis dependant upon the condition of the infraspinatus and the teres minor). In this regard, see the following: Boileau, P. et al. Grammont Reverse Prosthesis: Design, Rationale, and Biomechanics. JSES January/February: 147S-161S. 2005; Rittmeister, M. et al. Grammont Reverse Total Shoulder Arthroplasty in Patients with Rheumatoid Arthritis and Nonreconstructable Rotator Cuff Lesions. JSES. January/February: 17-22, 2001; Vanhove, B. Grammont's Reverse Shoulder Prosthesis for Rotator Cuff Arthropathy. A Retrospective Study of 32 Cases. Acta Orthop Belg. #70 (3): 219-225. 2004; Sirveaux, F. et al. Grammont inverted total shoulder arthroplasty in the treatment of glenohumeral osteoaitis with massive rupture of the cuff. JBJS 86-B: 388-395. 2004; Katzer, A. Two-Year Results After Exchange Shoulder Arthroplasty Using Inverse Implants. Orthopedics. Vol. 27, #11: 1165-1167. 2004; Walch, G. The Reverse Ball and Socket: When is it Indicated? Orthopaedics Today. pp. 18-20.

Of note, the Delta reverse shoulder is associated with a number of different types of complications including glenoid loosening, scapular "notching" (more descriptively called inferior glenoid erosion), acromion fractures, dislocation (head from poly and poly insert from humeral stem), instability, humeral stem fracture, humeral stem loosening, and glenoid screw fracture. In this regard, see the immediately preceding cited references.

BRIEF DESCRIPTION OF THE DRAWINGS

FIGS. 4E-4G show three more detailed perspective views of an example pear-shaped glenosphere according to an embodiment of the present invention;

FIGS. 9A-9C show: (1) the glenoid plate/compression screw/locking cap screw assembly of the embodiment of FIGS. 1A-1C; (2) detail of the compression screw/locking cap screw; and (3) detail of the compression screw/locking cap screw (wherein the locking cap screw is shown in phantom);

FIG. 40 shows a chart of effect of varying humeral neck angle on points of impingement (shaded data column third from right denotes typical Grammont design);

FIG. 41 shows a chart of effect of varying humeral constraint on ROM (middle shaded data column denotes typical Grammont design);

FIG. 42 shows a chart of effect of varying glenosphere thickness on ROM (middle shaded data column denotes typical Grammont design);

FIG. 43 shows a chart of effect of varying glenosphere diameter on jump distance (shaded data column second from left denotes typical Grammont design);

FIG. 58 shows a chart of comparison of ROM for an embodiment of the present invention and a typical Grammont Reverse shoulder prostheses.

Figures 1A, 1B, 1C:
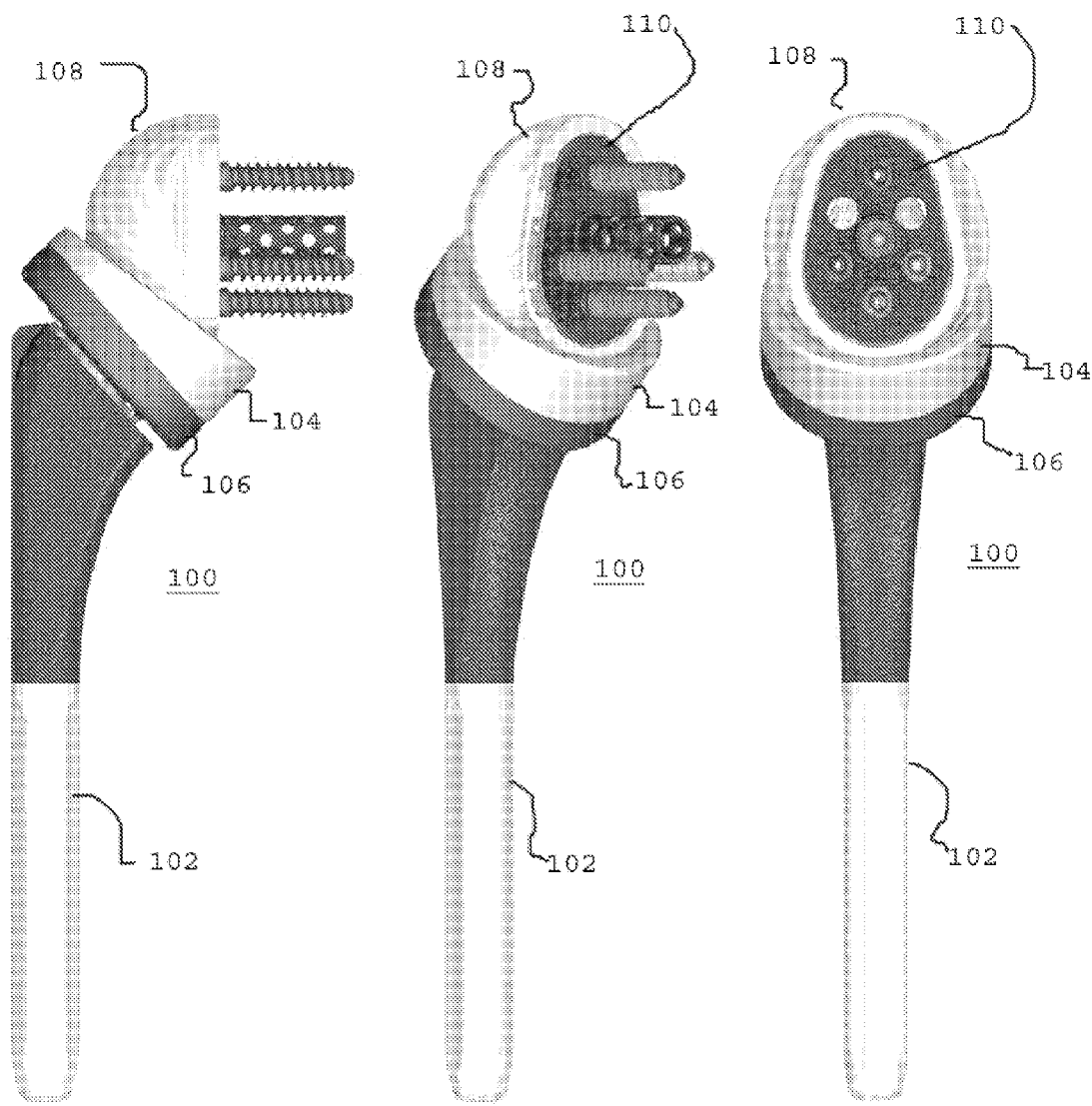
FIGS. 1A-1C show three perspective views of a reverse shoulder prosthesis (including glenosphere/glenoid plate assembly and humeral mating components) according to one embodiment of the present invention.
Figure 2:
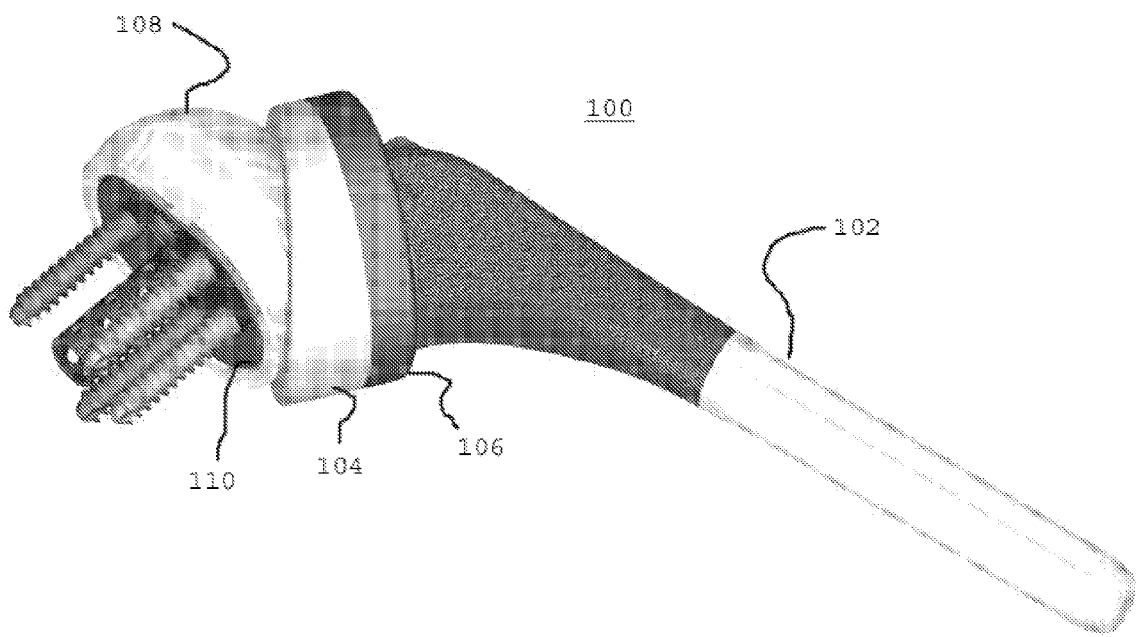
FIG. 2 shows another perspective view of the embodiment of FIGS. 1A-1C.

Among those benefits and improvements that have been disclosed, other objects and advantages of this invention will become apparent from the following description taken in conjunction with the accompanying figures. The figures constitute a part of this specification and include illustrative embodiments of the present invention and illustrate various objects and features thereof.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

Of note, various embodiments of the present invention are directed to a reverse shoulder prosthesis incorporating some or all of the aforementioned benefits associated with the Delta reverse shoulder design (while also aiming to minimize the number and rate of observed complications). These benefits of various embodiments of the present invention may include (but are not limited to): 1) lengthen/tension deltoid to improve muscle efficiency; 2) maintain center of rotation on the glenoid fossa to minimize the effective moment arm; and/or 3) invert the concavities of the natural joint to create a physical stop to prevent humeral head superior migration. The complications that various embodiments of the present invention may minimize include (but are not limited to): 1) eliminate impingement to reduce the degree of scapular notching and the incidence of dislocation; 2) improve glenoid fixation by increasing the number of available fixation points, positioning the fixation points in such a manner that it maximizes the potential for fixation (e.g., position the fixation points in such a manner that their location corresponds to the region of best quality/deepest bone in the native glenoid), allowing for all screws to be oriented/angled in any direction (to improve possibility of screw purchase), and/or allowing for any compression screw (regardless of its angular orientation) to be converted into a locking screw (to prevent the screws from backing out); 3) reduce glenoid osteolysis by improving stress transfer through the use of an anatomic shaped glenoid plate (e.g., the anatomic plate limits overhang on the A/P sides of the glenoid); and/or 4) improve stability and ROM by allowing the use of a larger diameter glenosphere (certain embodiments of the present invention may not require reaming of the proximal humerus, as is typically required in the Grammont design . . . often the proximal humerus establishes the size of the glenosphere based upon the maximum size of liner that can be placed).

Referring now to FIGS. 1A-1C and 2, various views of an assembled construct 100 according to an embodiment of the present invention are shown. The components of this construct may include: a humeral stem 102 (which may be used in either pressfit or cemented applications and may be constructed, for example, from titanium); a humeral liner 104 (a concave component which mates with the convex glenosphere, this element may be constructed, for example, from UHMWPE); a humeral adapter plate 106 (which connects the humeral liner to the humeral stem, this element may be constructed, for example, from titanium); a glenosphere 108 (this element may be constructed, for example, from cobalt chrome); a pear-shaped glenoid plate 110 (this element may be constructed, for example, from titanium); and a number of screws and fixation devices for assembly of the individual components to one another and for assembly of the construct to the native bone (these elements may be constructed, for example, from titanium). Of note, the glenoid plate of this example is pear-shaped.

Figures 3A, 3B, 3C:
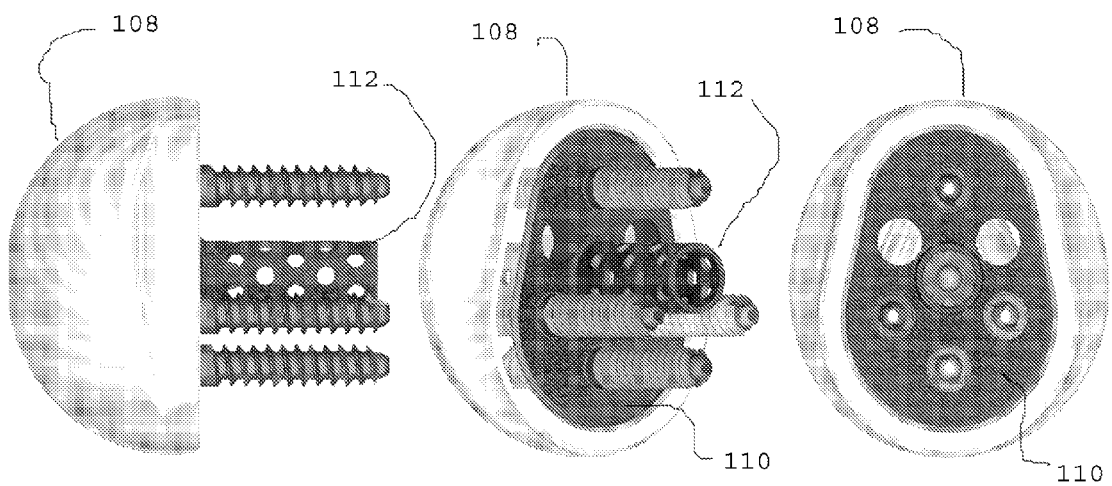
FIGS. 3A-3C show three more detailed perspective views of the glenosphere/glenoid plate assembly of the embodiment of FIGS. 1A-1C.
Figures 4A, 4B, 4C, 4D:
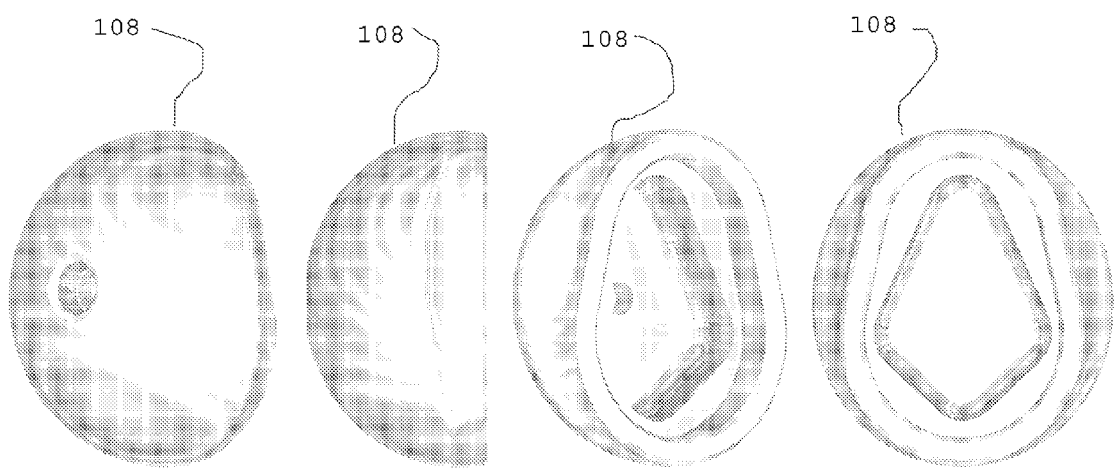
FIGS. 4A-4D show four more detailed perspective views of the glenosphere of the embodiment of FIGS. 1A-1C (the glenosphere of this example is a 38 mm glenosphere)

Referring now to FIGS. 3A-3C, more detailed views of the glenosphere/glenoid plate assembly of FIGS. 1A-1C and 2 are shown (stem 112 is seen clearly in these Figs.).

Referring now to FIGS. 4A-4D, more detailed views of the glenosphere of FIGS. 1A-1C and 2 are shown (note that the glenosphere may be hollowed out to reduce weight).

Referring now to FIGS. 4E-4G, detailed views of another example glenosphere are shown (note that the glenosphere may be hollowed out to reduce weight).

Figures 5A, 5B, 5C:
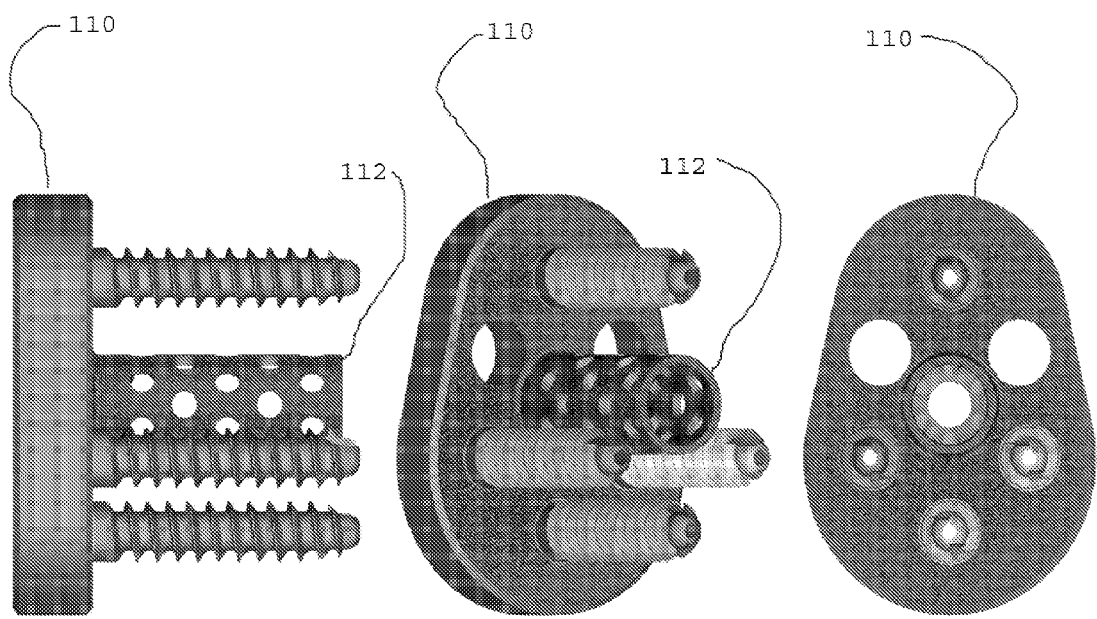
FIGS. 5A-5C show three more detailed perspective views of the pear-shaped glenoid plate of the embodiment of FIGS. 1A-1C (showing a stem provided with holes for bone "through growth")

Referring now to FIGS. 5A-5C, more detailed views of the pear shaped glenoid plate of FIGS. 1A-1C and 2 are shown. In this regard, several features should be noted: 1) the 6 screw holes on the backside of the plate; and 2) the bone "trough-growth" cage stem which enables bone graft to be injected (e.g., via syringe) through the front of the plate and/or placed through the hole in the bottom surface of the cage stem).

Figures 5D, 5E, 5F:
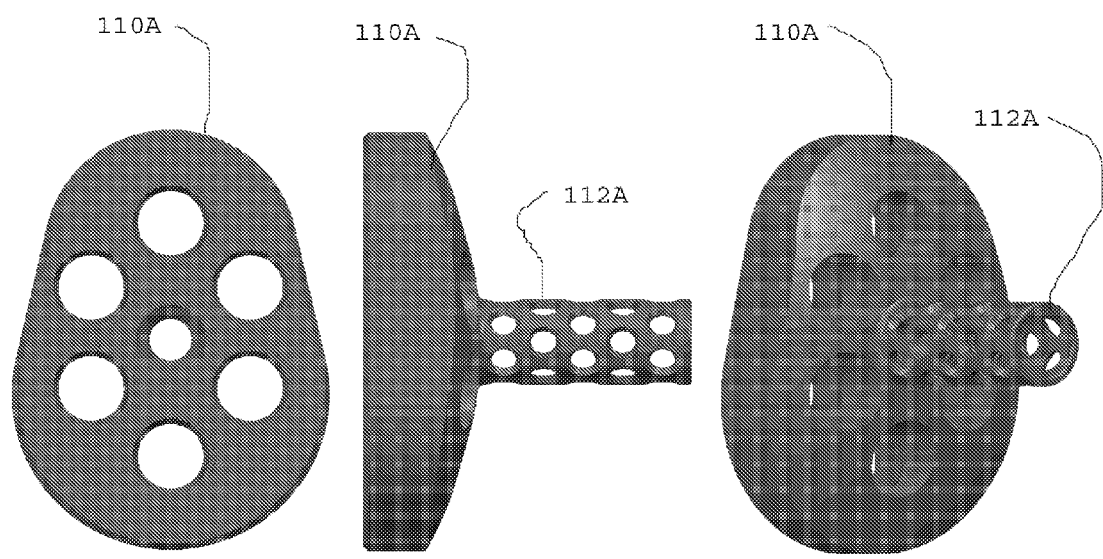
FIGS. 5D-5F show three more detailed perspective views of another example pear-shaped glenoid plate according to an embodiment of the present invention (showing a stem provided with holes for bone "Through growth")

Referring now to FIGS. 5D-5F, detailed views of another example pear-shaped glenoid plate 110A are shown.

Figure 6:
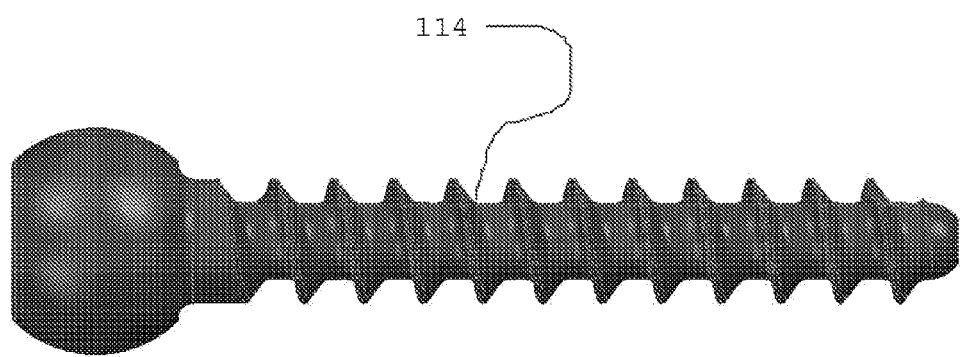
FIG. 6 shows a perspective view of an example compression screw of the type which may be utilized with the present invention.

Referring now to FIG. 6, a compression screw 114 according to an embodiment of the present invention is shown (note the spherical head which enables the screw to be angularly oriented within glenoid plate 110 (e.g., up to 17.5 degrees) in any desired direction—in one specific example, the holes in glenoid plate 110 may have corresponding concavities).

Figure 7A:
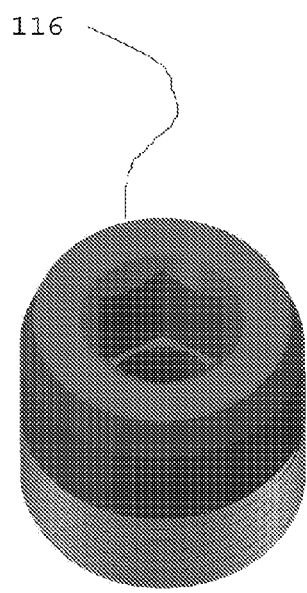
FIGS. 7A-7C show three perspective views of an example locking cap screw of the type which may be utilized with the present invention.
Figure 7B:
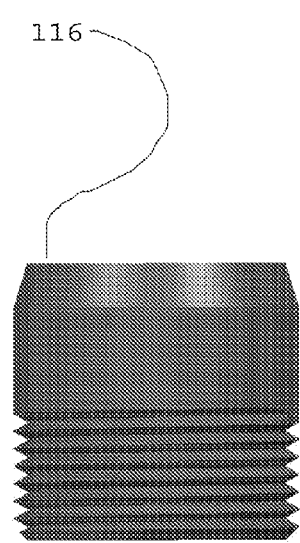
Figure 7C:
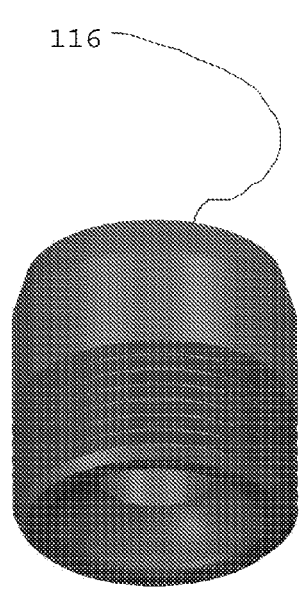
Figures 7D, 7E, 7F:
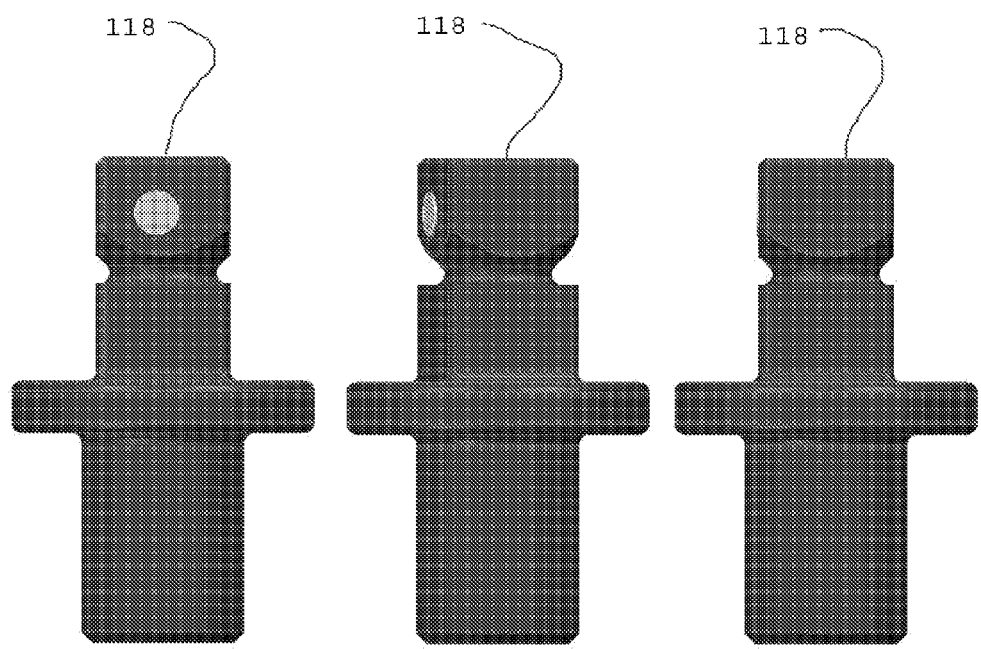
FIGS. 7D-7F show three views of an example torque defining screw driving element which may be utilized with the present invention.

Referring now to FIGS. 7A-7C, a locking cap screw 116 according to an embodiment of the present invention is shown (a locking cap screw may screwed into the glenoid plate on top of a compression screw to prevent the compression screw from backing out and/or to lock the compression screw in a desired angular orientation—see FIGS. 8A, 8B, and 9A-9C). Further, FIGS. 7D-7F show three views of a torque defining screw driving element 118 which may be utilized with the present invention (e.g., to drive a screw and/or locking cap with a predefined amount of torque (e.g., by breaking when the predefined amount of torque is applied)).

Figures 8A, 8B:
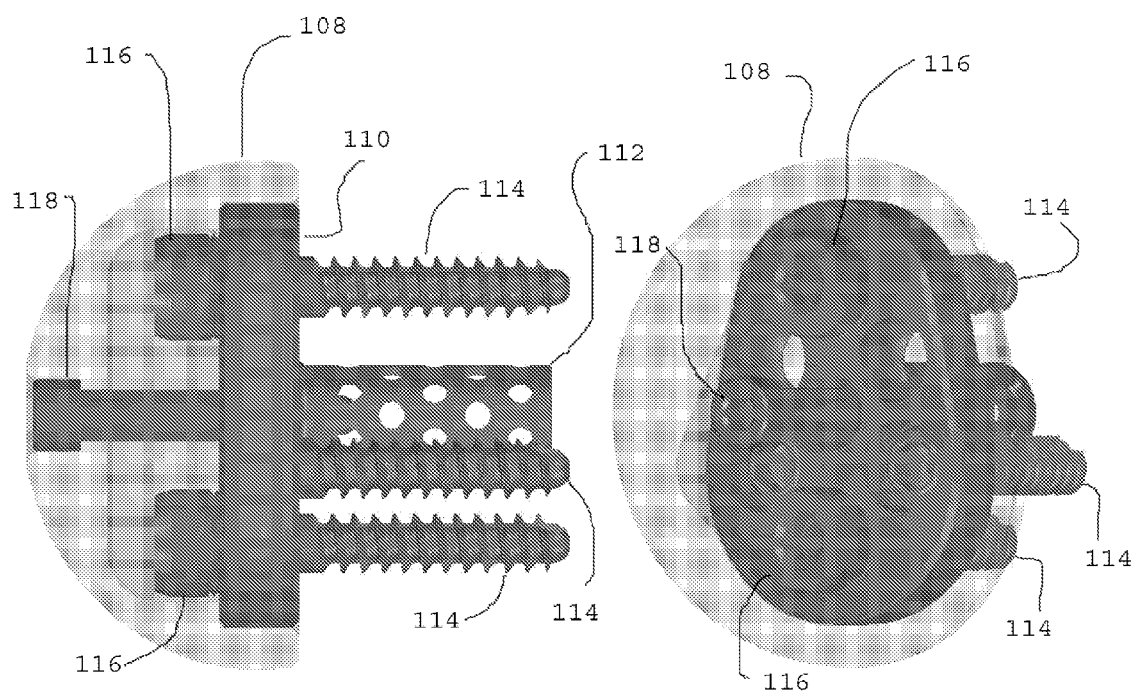
FIGS. 8A and 8B show two views of the glenosphere/glenoid plate assembly of the embodiment of FIGS. 1A-1C (wherein the glenosphere is shown in phantom)

Referring now more particularly to FIGS. 8A and 8B, more detailed views demonstrating how the compression screw 114 and locking cap screw 116 mate with the glenoid plate 110 are shown. These FIGS. 8A and 8B also show how glenosphere 108 (depicted here in phantom form) may be assembled to glenoid plate 110 via use of assembly bolt 118. FIGS. 9A-9C further clarify the relationship of the compression screw 114 and locking cap screw 116 to the glenoid plate 110. These FIGS. 9A-9C also detail the spherical articulation between the compression screw 114 and locking cap screw 116—a feature which enables the compression screw 114 to be locked regardless of its angular orientation.

Figures 10A, 10B, 10C:
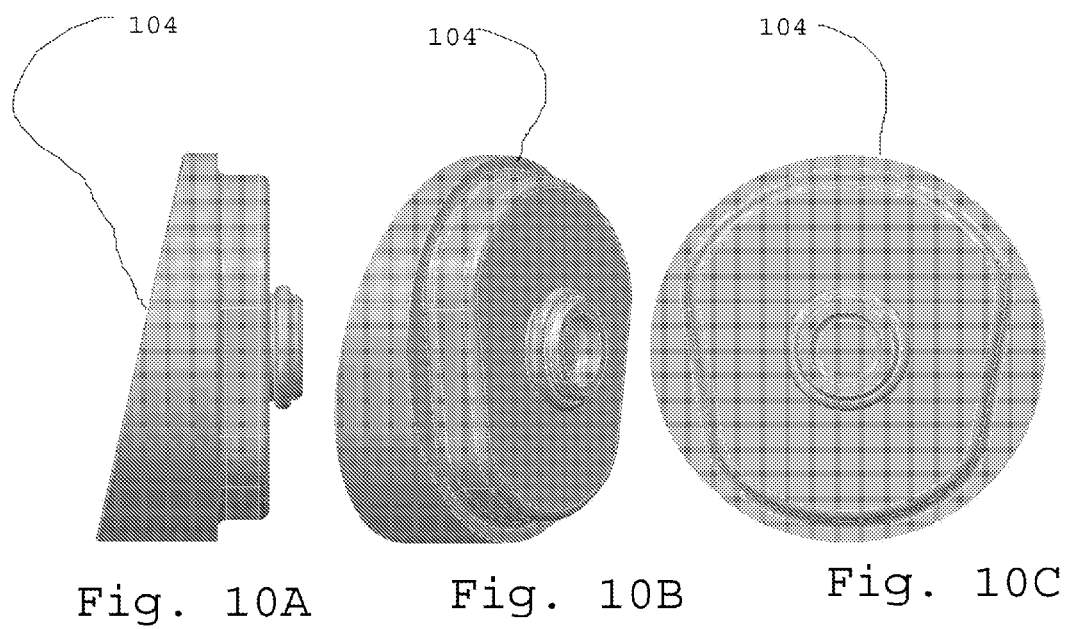
FIGS. 10A-10C show three views of a reverse shoulder humeral liner according to an embodiment of the present invention.
Figure 11A:
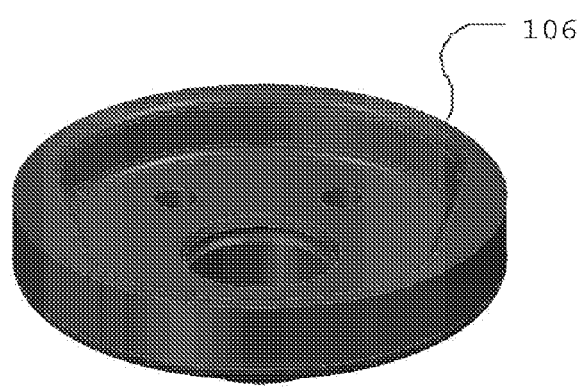
FIGS. 11A-11E show five views of a reverse shoulder humeral plate according to an embodiment of the present invention.
Figure 11B:
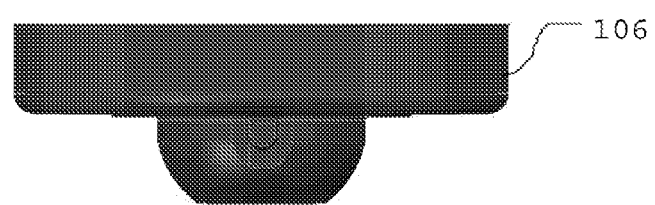
Figure 11C:
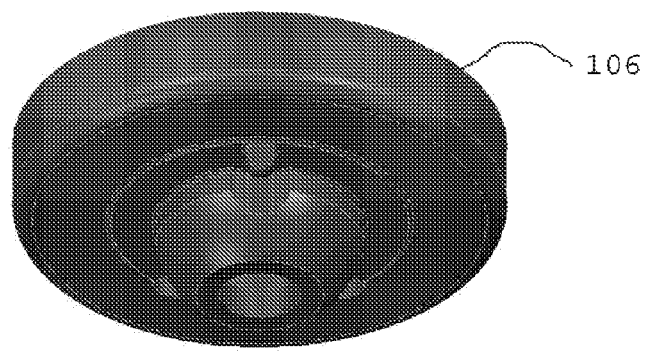
Figures 11D, 11E:
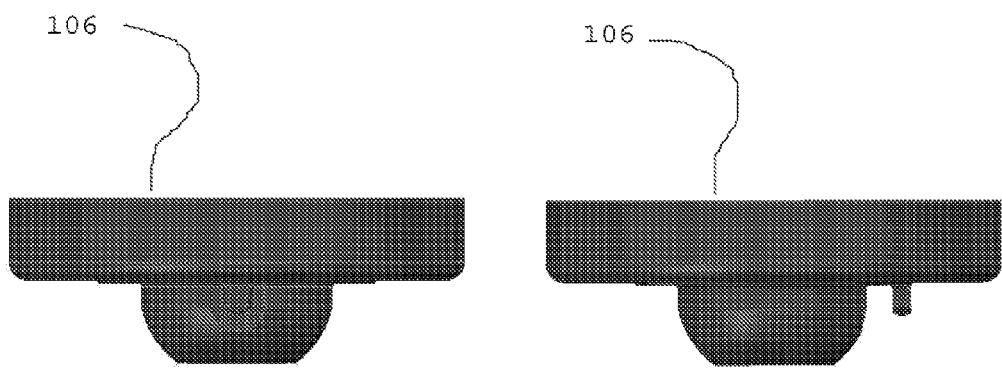

Referring now to FIGS. 10A-10C, three views of humeral liner 104 of FIGS. 1A-1C and 2 are show.

Referring now to FIGS. 11A-11E, five views of humeral plate 106 of FIGS. 1A-1C and 2 are show.

Referring now to FIGS. 16A-16D, various views of an assembled construct 1600 according to an embodiment of the present invention are shown. The components of this construct may include: a humeral stem 1602 (which may be used in either pressfit or cemented applications and may be constructed, for example, from titanium); a humeral liner 1604 (a concave component which mates with the convex glenosphere, this element may be constructed, for example, from UHMWPE); a humeral adapter plate 1606 (which connects the humeral liner to the humeral stem, this element may be constructed, for example, from titanium); a glenosphere 1608 (this element may be constructed, for example, from cobalt chrome); an oval-shaped glenoid plate 1610 (this element may be constructed, for example, from titanium); and a number of screws and fixation devices for assembly of the individual components to one another and for assembly of the construct to the native bone (these elements may be constructed, for example, from titanium). Of note, the glenoid plate 1610 of this example is oval-shaped.

Referring now to FIGS. 17A-17D, more detailed views of the oval-shaped glenoid plate of FIGS. 16A-16D are shown (stem 1612 is seen clearly in these Figs.).

Referring now to FIGS. 18A-18D, more detailed views of another example oval-shaped glenoid plate 1610A are shown (stem 1612A is non-cylindrical in these Figs.).

Referring now to FIGS. 19A-19D, more detailed views of the glenosphere of FIGS. 16A-16D are shown (note that the glenosphere may be hollowed out to reduce weight).

Figures 20A, 20B:
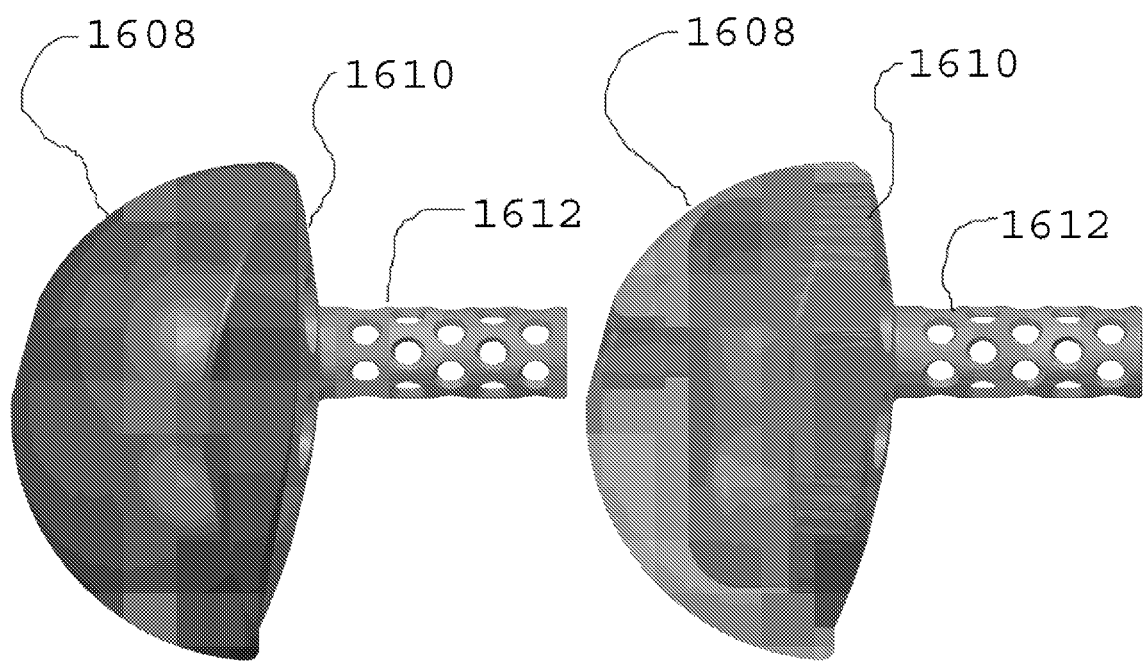
FIGS. 20A and 20B show two views of the glenosphere/glenoid plate assembly of the embodiment of FIGS. 16A-16D (wherein the glenosphere is shown in phantom in FIG. 20B and wherein the glenosphere of this example is a 38 mm glenosphere)
Figures 21A, 21B, 21C, 21D:
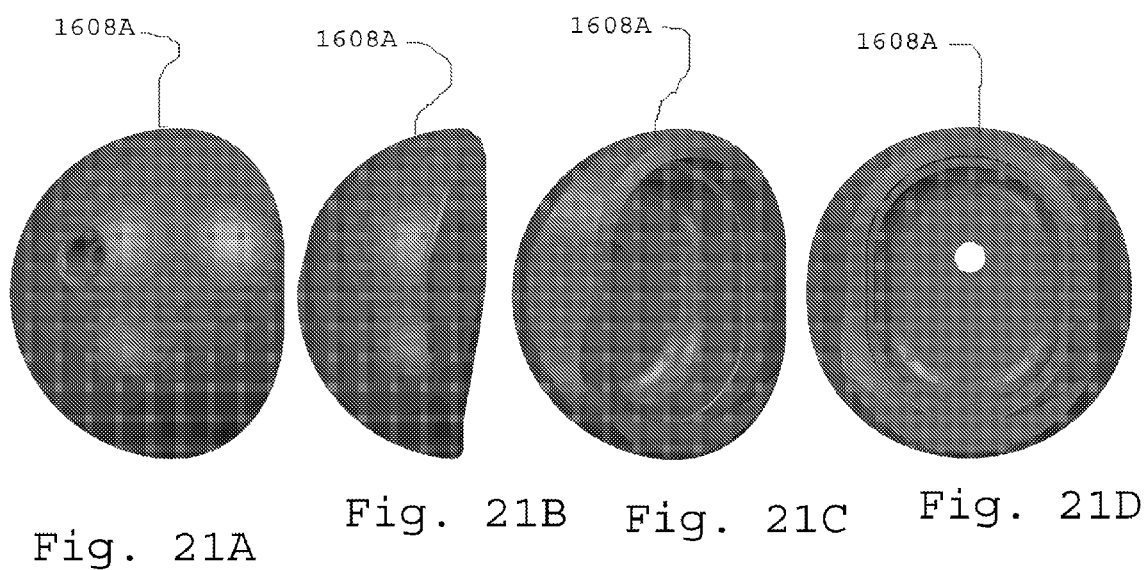
FIGS. 21A-21D show four more detailed perspective views of an example oval-shaped glenosphere of an embodiment of the present invention (the glenosphere of this example is a 42 mm glenosphere)

Referring now to FIGS. 20A-20B, more detailed views of the glenoid plate/glenosphere assembly of FIGS. 16A-16D are shown (the glenosphere of FIG. 20B is shown in phantom form).

Referring now to FIGS. 21A-21D, more detailed views of another example glenosphere are shown.

Figures 22A, 22B:
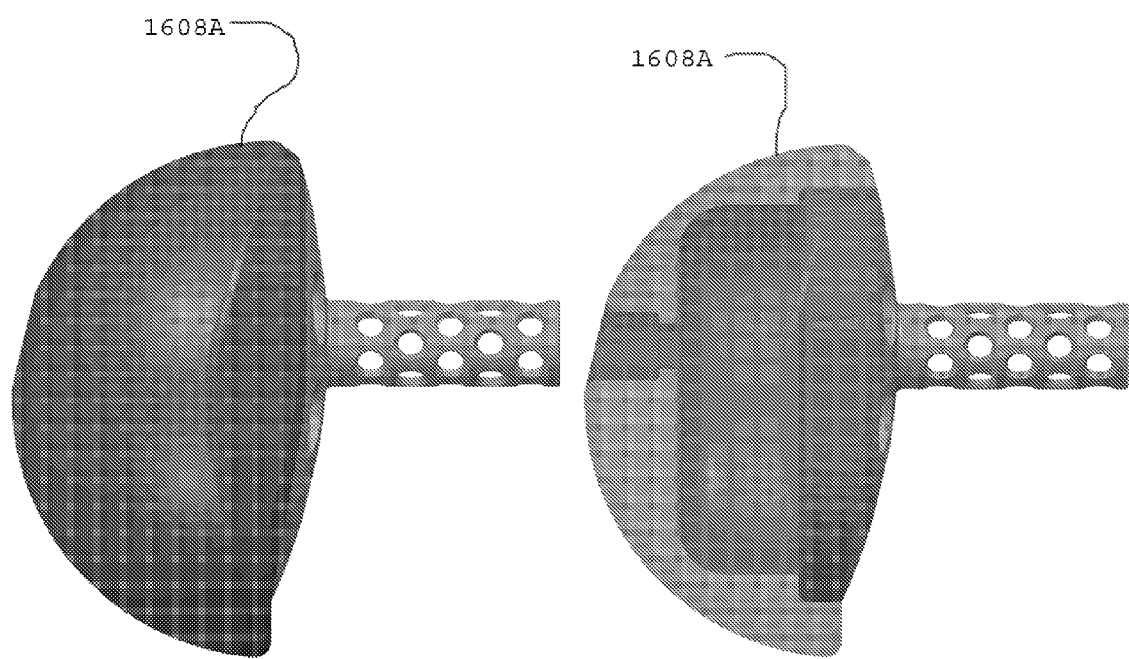
FIGS. 22A and 22B show two views of an oval-shaped glenosphere/glenoid plate assembly of an embodiment of the present invention (wherein the glenosphere is shown in phantom in FIG. 22B and wherein the glenosphere of this example is a 38 mm glenosphere)
Figures 23A, 23B, 23C, 23D:
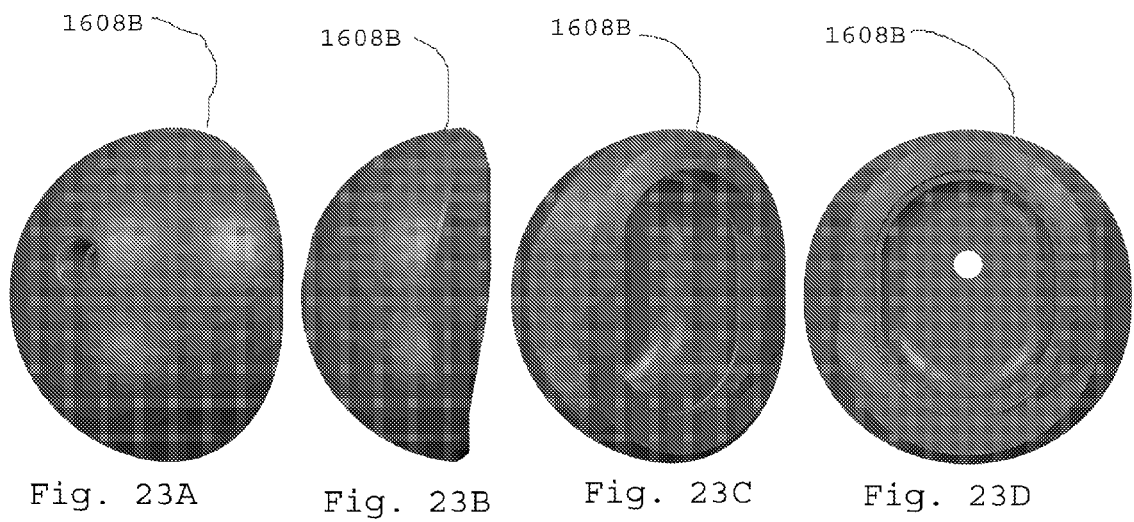
FIGS. 23A-23D show four more detailed perspective views of an example glenosphere of an embodiment of the present invention (the glenosphere of this example is a 46 mm glenosphere)

Referring now to FIGS. 22A-22B, more detailed views of an example glenoid plate/glenosphere assembly are shown (the glenosphere of FIG. 22B is shown in phantom form).

Referring now to FIGS. 23A-23D, more detailed views of another example glenosphere are shown.

Figures 24A, 24B:
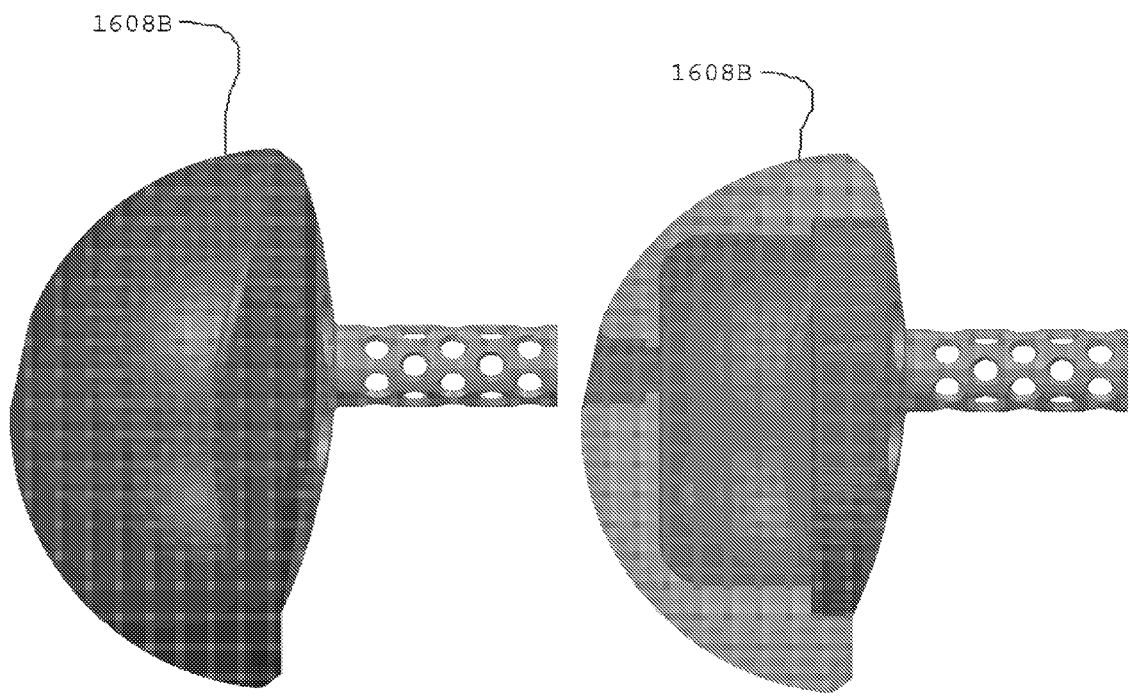
FIGS. 24A and 24B show two views of an glenosphere/glenoid plate assembly of an embodiment of the present invention (wherein the glenosphere is shown in phantom in FIG. 24B and wherein the glenosphere of this example is a 42 mm glenosphere)

Referring now to FIGS. 24A-24B, more detailed views of an example glenoid plate/glenosphere assembly are shown (the glenosphere of FIG. 24B is shown in phantom form).

Figure 25:
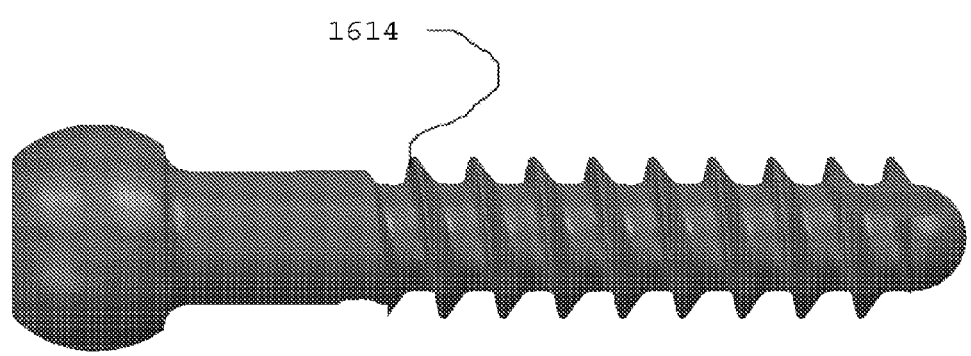
FIG. 25 shows a perspective view of an example compression screw of the type which may be utilized with the present invention.

Referring now to FIG. 25, a compression screw 1614 according to an embodiment of the present invention is shown (note the spherical head which enables the screw to be angularly oriented within glenoid plate 1610 (e.g., up to 17.5 degrees) in any desired direction—in one specific example, the holes in glenoid plate 1610 may have corresponding concavities).

Of course, it should be noted that there are other embodiments of the invention and/or of the individual components comprising the invention, including (but not limited to) various shapes, sizes, and materials. For example (which example is intended to be illustrative and not restrictive), the materials of the humeral liner and glenosphere could be inverted (reverse designs typically have a metal glenosphere/glenoid plate and a plastic humeral liner—an alternative embodiment is a metal humeral liner and a plastic glenosphere)—doing so could theoretically reduce the weight cyclically imposed on the native glenoid bone (by eliminating many of the much heavier metal components). This may also reduce the cost of the device by eliminating the need for multiple metal screws and fixation components. In another example (which example is intended to be illustrative and not restrictive), if both the glenosphere and glenoid plate were manufactured of plastic then the device could be used exclusively in cemented applications—an application that has been shown to be the standard of care in traditional shoulder arthroplasty. Conversely, both the humeral liner and the glenosphere/plate could be manufactured from the same material then a metal-on-metal (or ceramic-on-ceramic) articulation could be achieved (which have been shown to produce less wear in hip arthroplasty applications and as a result have a lower incident of osteolysis). In yet another example (which example is intended to be illustrative and not restrictive), the glenoid plate design may have a central screw rather than a central cage stem (the central screw hole could be advantageous in cases in which a central bone defect exists; the screw could be oriented in various directions to ensure that screw purchase is obtained).

Of note, various embodiments of the present invention may offer a number of advantages over the prior art—some of these advantages are described above. FIGS. 12-15 further elaborate on some of these advantages.

Figure 12:
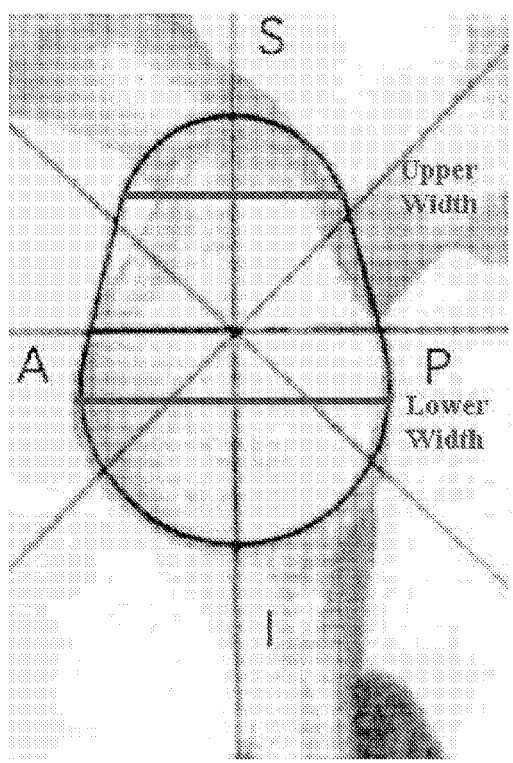
FIG. 12 shows an outline of a pear-shaped glenoid and results from 2 anatomic studies: Iannotti, J. P. et al. The Normal Glenohumeral Relationships. JBJS. Vol. 74-A, #4: 491-500 1992 and Checroun, A. J. et al. Fit of Current Glenoid Component Designs: an Anatomic Cadaver Study. JSES. Vol. 11, #6: 614-617. 2002 (image modified from Checroun)

More particularly, FIG. 12 summarizes the results of two different anatomic studies (see Iannotti, J. P. et al. The Normal Glenohumeral Relationships. JBJS. Vol. 74-A, #4: 491-500. 1992 and Checroun, A. J. et al. Fit of Current Glenoid Component Designs: an Anatomic Cadaver Study. JSES. Vol. 11, #6: 614-617. 2002)—each of these studies demonstrate that the glenoid is wider inferiorly than superiorly and that it has a characteristic pear or "inverted-comma" shape.

Figure 13:
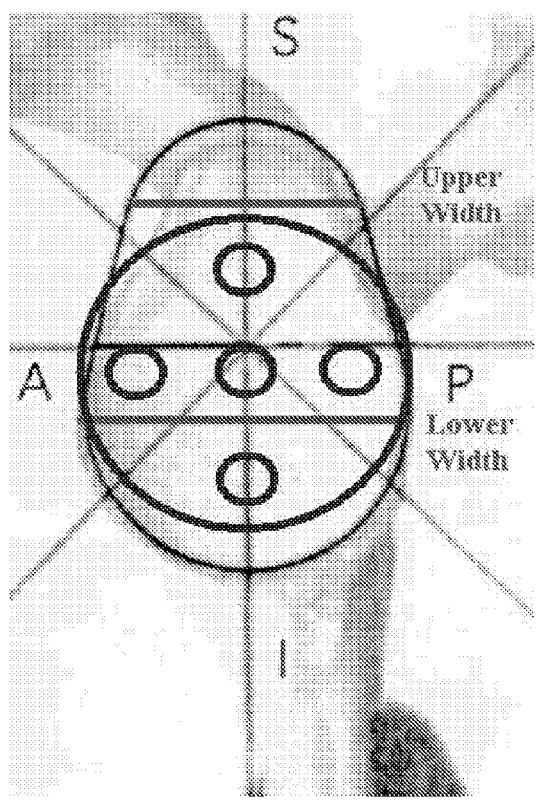
FIG. 13 shows the fit of a conventional reverse glenosphere plate on glenoid (image modified from Checroun, A. J. et al. Fit of Current Glenoid Component Designs: an Anatomic Cadaver Study. JSES. Vol. 11, #6: 614-617. 2002)
Figure 13:
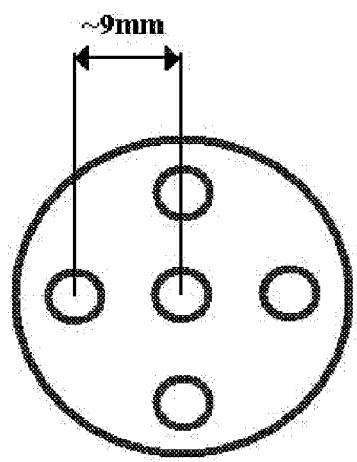

Further, FIG. 13 graphically illustrates the fit of a traditional Grammont-style glenoid plate on a representative glenoid fossa; it is believed that the typical 4-quadrant location of the screw holes is not ideal due to the anterior and posterior slope of the scapula—this slope results in a thin base of bone in these locations.

Figure 14:
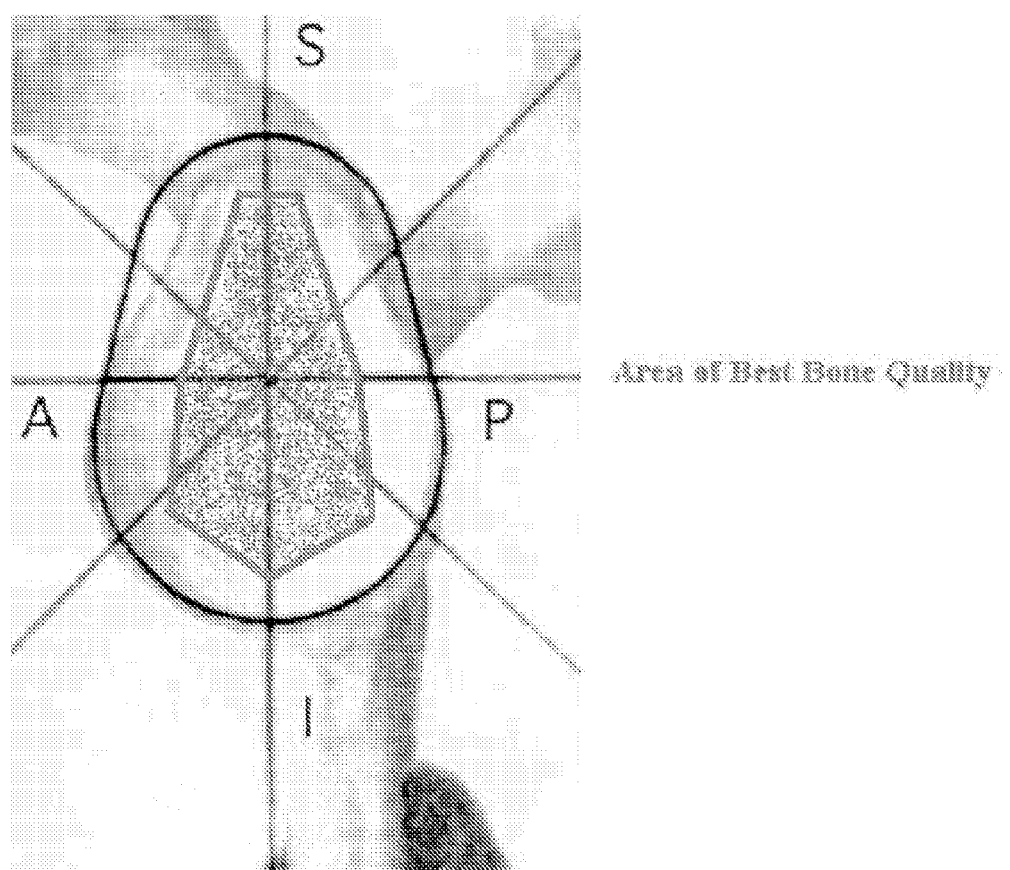
FIG. 14 shows an area of best quality/deepest glenoid bone (image modified from Checroun, A. J. et al. Fit of Current Glenoid Component Designs: an Anatomic Cadaver Study. JSES. Vol. 11, #6: 614-617. 2002)

Further still, FIG. 14 graphically illustrates the region of best quality/deepest bone in the native glenoid.

Figure 15:
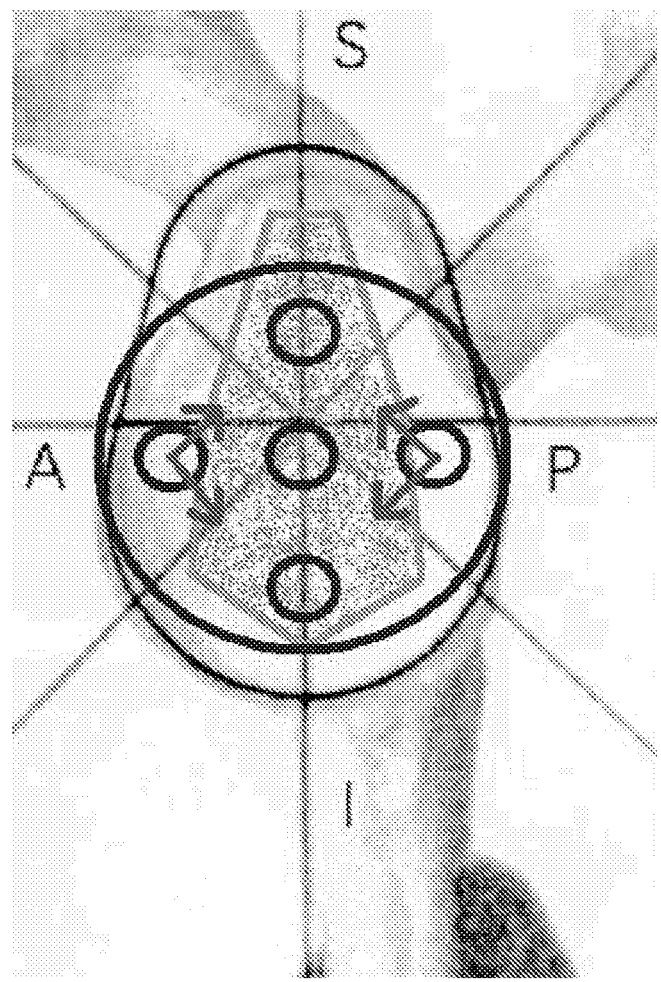
FIG. 15 shows a theoretical improvement in probability of A/P bone-screw purchase if hole pattern is modified as shown according to an embodiment of the present invention (image modified from Checroun, A. J. et al. Fit of Current Glenoid Component Designs: an Anatomic Cadaver Study. JSES. Vol. 11, #6: 614-617. 2002)
Figures 16A, 16B, 16C, 16D:
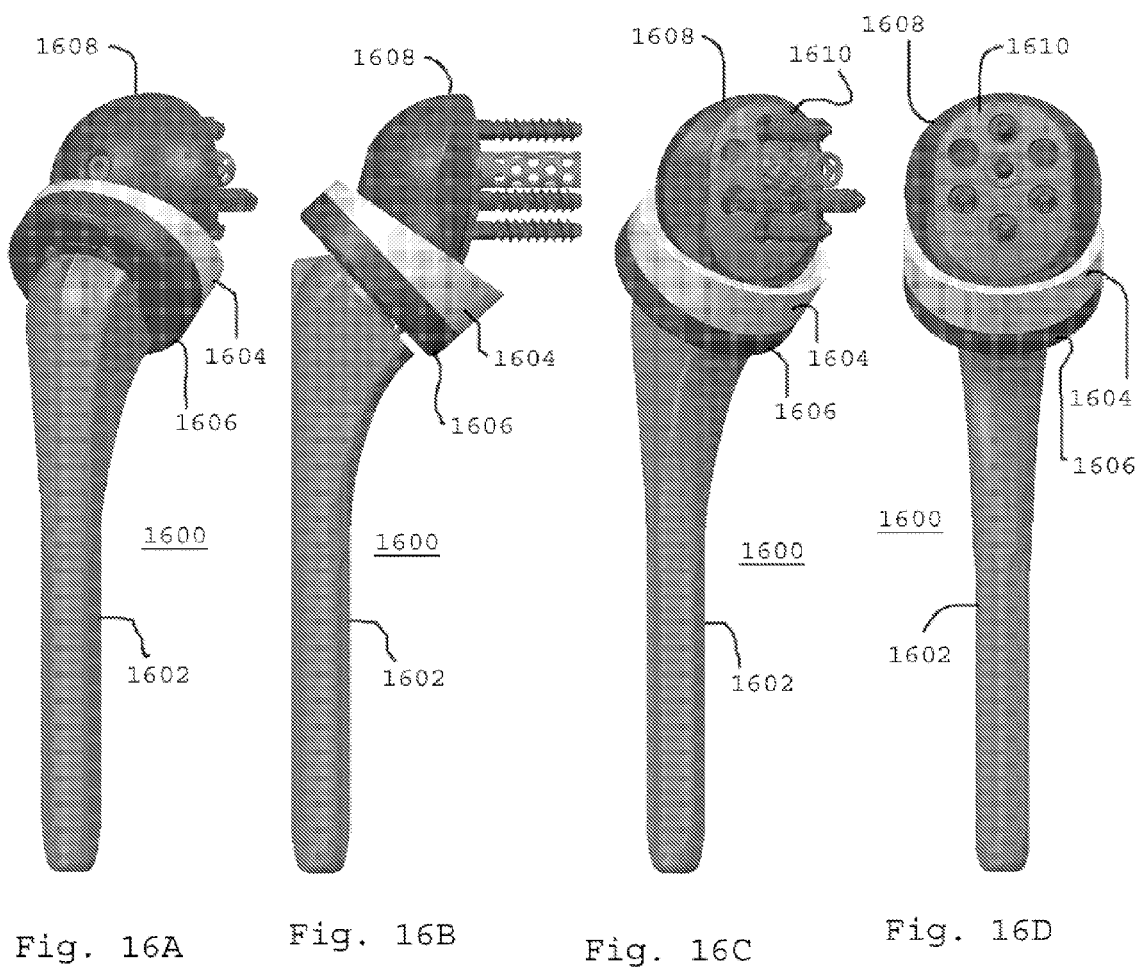
FIGS. 16A-16D show four perspective views of a reverse shoulder prosthesis (including glenosphere/glenoid plate assembly and humeral mating components) according to an embodiment of the present invention.
Figures 17A, 17B, 17C, 17D:
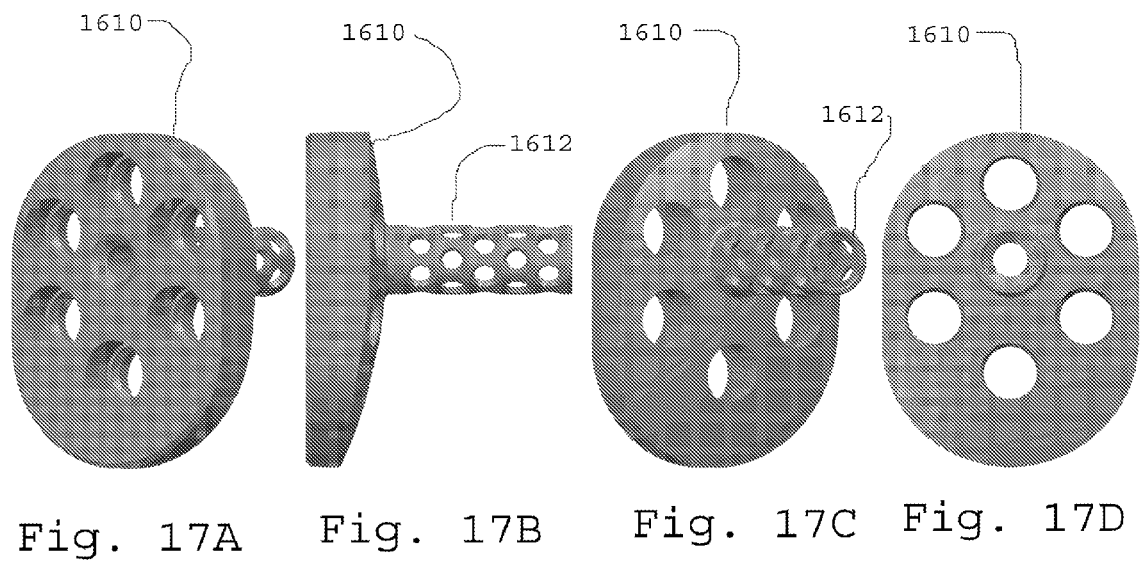
FIGS. 17A-17D show four more detailed perspective views of the oval-shaped glenoid plate of the embodiment of FIGS. 16A-16D (showing a superiorly-shifted stem provided with holes for bone "through growth")
Figures 18A, 18B, 18C, 18D:
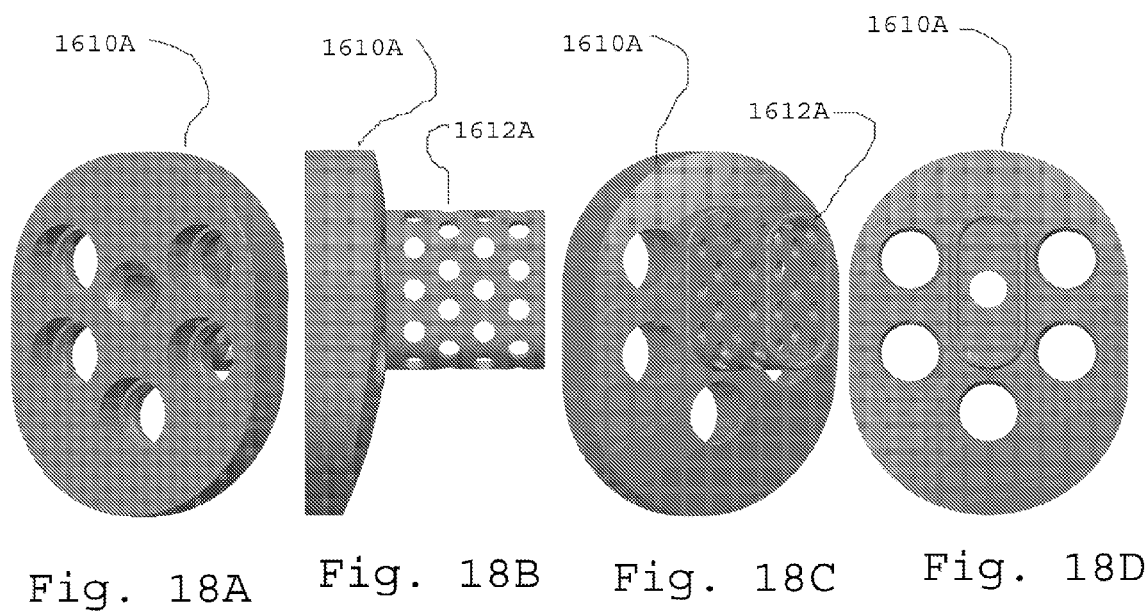
FIGS. 18A-18D show four more detailed perspective views of another example of an oval-shaped glenoid plate of an embodiment of the present invention (showing a superiorly-shifted non-cylindrical stem provided with holes for bone "through growth")
Figures 19A, 19B, 19C, 19D:
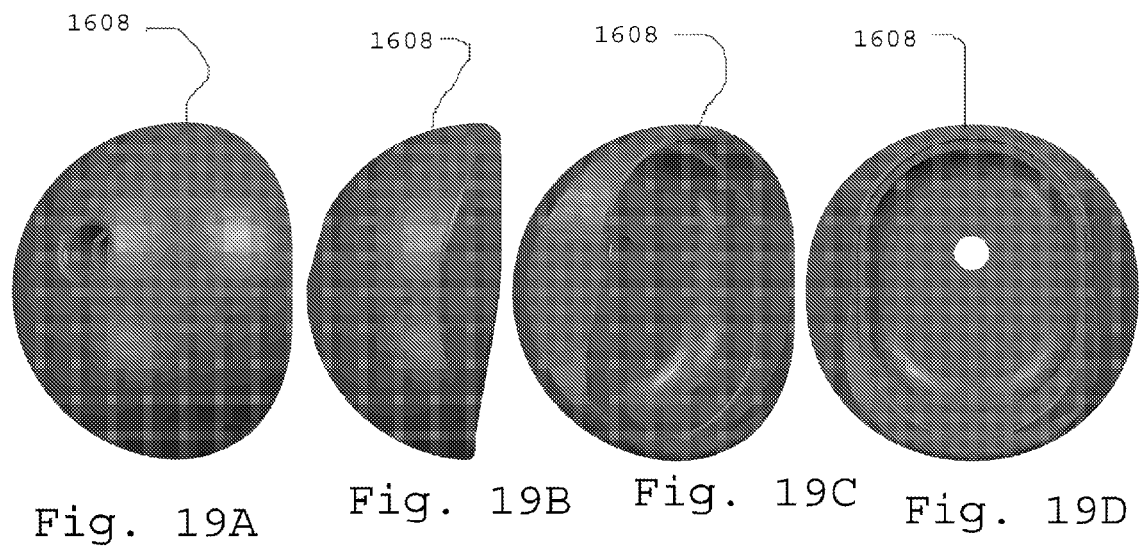
FIGS. 19A-19D show four more detailed perspective views of the glenosphere of the embodiment of FIGS. 16A-16D (the glenosphere of this example is a 38 mm glenosphere)

Finally, FIG. 15 graphically illustrates the rationale for screw hole position utilized in an embodiment of the present invention.

In other examples (which examples are intended to be illustrative and not restrictive), the present invention may be constructed as follows:

Reverse Shoulder Glenoid Plate
Material: Machined from Wrought Ti-6Al-4V
Scope: 1 Size (used with 38, 42, and 46 mm Glenosphere);
Dimensions/Features: 29 mm diameter, 5 mm taper, 20 mm length bone "through growth" cage, each screw hole has a spherical base allowing the compression screws to be angled 15°, each hole also has a threaded portion for attachment of a locking cap screw.

Reverse Shoulder Glenosphere
Material: Machined from Cast Co—Cr
Scope: 3 Sizes (38/22 mm, 42/24 mm, and 46/26 mm Diameter and Thickness)
Dimensions/Features: Glenosphere hollowed out to reduce weight Reverse Shoulder Humeral Liner
Material: Machined from Compression Molded UHM-WPE Bar (Enhanced Poly: Connection GXL)
Scope: 3 Diameters (38, 42, and 46 mm Liners); Multiple offsets
Dimensions/Features: Connection to humeral plate configured for rotational stability (e.g., "mushroom" or other non-circular shape).

Reverse Shoulder Humeral Plate
Material: Machined from Wrought Ti-6Al-4V
Scope: 3 Sizes (38, 42, and 46 mm)
Dimensions/Features: Connection to liner configured for rotational stability (e.g., "mushroom" shaped or other non-circular shape); male pin(s) may connect to humeral stem for rotational stability Reverse Shoulder Compression Screw
Material: Machined from Ti-6Al-4V or SS Alloy
Scope: 1 diameter (4.0 mm) at multiple lengths
Dimensions/Features: Spherical head for insertion at a variable angle (e.g., up to 15°); cannulated Reverse Shoulder Locking Cap Screw
Material: Machined from Ti-6Al-4V or SS Alloy
Scope: 1 size (~9 mm long, 8 mm wide)
Dimensions/Features: Locks compression screws to glenoid plate at any angle; cannulated; fits in hollowed out space of glenosphere.

Glenosphere Locking Screw
Material: Machined from Ti-6Al-4V or SS Alloy
Scope: 1 size (~25 mm long, 4 mm wide)
Dimensions/Features: Locks glenosphere to glenoid plate.

Reverse Shoulder Torque Defining Screw Driving Element
Material: Machined from wrought Ti-6Al-4V; UHMWPE plug
Scope: 1 Size; minimum cross section as required
Dimensions/Features: Design Utilizes poly plug to retain square head after fracture According to another example (which example is intended to be illustrative and not restrictive), the present invention may provide for:

The reverse prosthesis may be integrated with the primary system—may retain the primary stem for revision (which is beneficial because 30% of reverse shoulders are implanted as revisions). Additionally, the prosthesis may use existing humeral implant inventory, existing humeral instrumentation, and/or a similar surgical technique (e.g., may maintain a 132.5° humeral osteotomy).

As described by the ROM study (see Table 1, below), the reverse prosthesis may be associated with a 16.7% to 18.9% increase in ROM (as compared to the traditional Grammont prosthesis).

As described by the ROM study (see Table 1, below), the reverse prosthesis may be associated with a reduction in the incidence of scapular notching (i.e. medial/inferior impingement of humerus on scapula) as a result of the reduction in neck angle from 155° to 145° (as compared to the traditional Grammont design) and the increase in humeral liner size (since the liner may be brought out of the proximal humerus.

The reverse prosthesis may maintain the low incidence of glenosphere loosening by utilizing the proven traditional Grammont-style glenosphere/screw/baseplate designs (note: the glenosphere design may be hollowed out to reduce weight).

The glenoid plate may utilize a bone "Through-growth" cage design to enhance fixation.

The glenoid plate may allow for the insertion of a compression screw (e.g., at up to 15 degrees of angular variability) in any of the 4 holes to maximize bone purchase.

The glenoid plate may allow the use of a locking cap screw which can be attached to any compression screw thereby making each screw a locking/compression screw.

The humeral liner may be manufactured from Connection GXL (i.e. enhanced poly) and may utilize a "mushroom" apical-locking mechanism to attach the humeral liner to the humeral plate (see FIGS. 10A-10C showing three views of such an example humeral liner and FIGS. 11A-11E showing five views of such an example humeral plate)—therefore, a low incidence of humeral liner wear and disassociation may be expected.

TABLE 1

Reverse Shoulder ROM Comparison

| Glenosphere Diameter/ Thickness | Neck Angle | Degree of Constraint | Lateral Offset (inches) | Jump Distance (inches) | ROM Range (w/o scapular motion) | Total ROM (w/scapular motion of 1.5) | Total ROM (w/scapular rotation, 15° Correction) | Percent Increase in ROM over Grammont | Glenosphere Weight (grams) |
|---|---|---|---|---|---|---|---|---|---|
| 38/22 mm | 145° | 0.312 | 0.893 | 0.323 inches at 55° Abd | 17 to 83° | 112.9° | 135° | 16.7% | 65 |
| 42/24 mm | 145° | 0.300 | 0.944 | 0.334 inches at 55° Abd | 13 to 87° | 116.6° | 136.9° | 17.8% | 98 |
| 46/26 mm | 145° | 0.288 | 0.969 | 0.341 inches at 55° Abd | 11 to 90° | 120.8° | 138.8° | 18.9% | 140 |
| Grammont 36/18 mm | 155° | 0.276 | 0.584 | 0.330 inches at 65° Abd | 35 to 95° | 90° | 112.5° | NA | 47 |

Another embodiment of the present invention relates to a reverse shoulder prosthesis and method for implantation that incorporates many or all of the aforementioned benefits associated with the traditional Grammont reverse shoulder design while at the same time minimizing the number and rate of observed complications and to address other areas of concern related to the method of implantation. The historic benefits which may be incorporated include (but are not limited to): 1) lengthen/tension deltoid to improve muscle efficiency; 2) maintain center of rotation on (or close to) the glenoid fossa to minimize the effective moment arm; and/or 3) invert the concavities of the natural joint to create a physical stop to prevent humeral head superior migration. The complications/ concerns that are minimized include (but are not limited to): 1) reduce the incidence of impingement; 2) reduce the incidence of scapular notching; 3) improve stability; 4) decrease the incidence of dislocation; 5) improve glenoid fixation; 6) conserve bone; and/or 7) better facilitate a conversion of a hemi- or total shoulder to a reverse shoulder. A detailed description of each design feature which may address the aforementioned complications/concerns is disclosed below.

Figure 26:
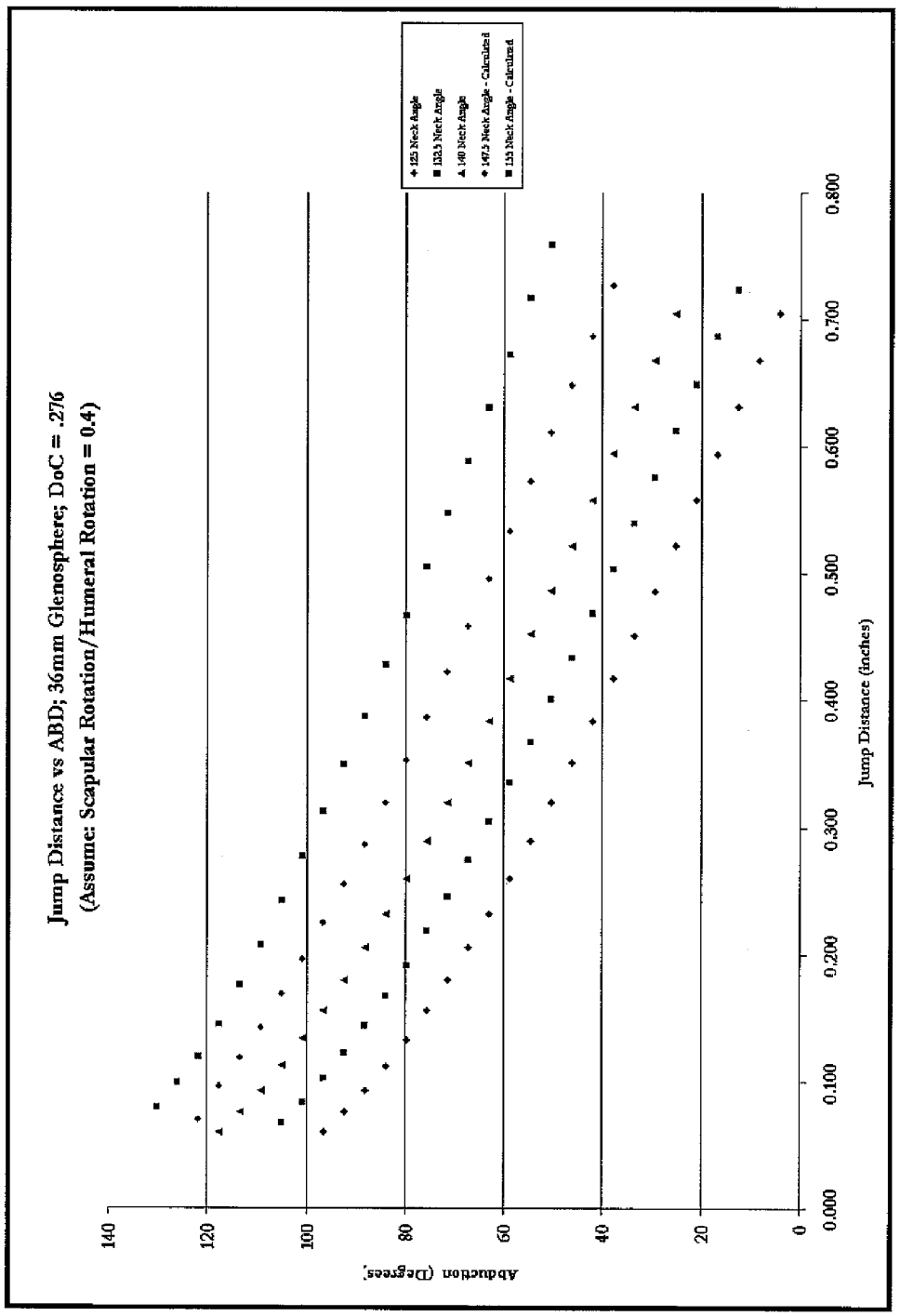
FIG. 26 is a graph showing testing results demonstrating that a 10° reduction in neck angle results in a downward shift in range of motion (ROM)
Figure 27:
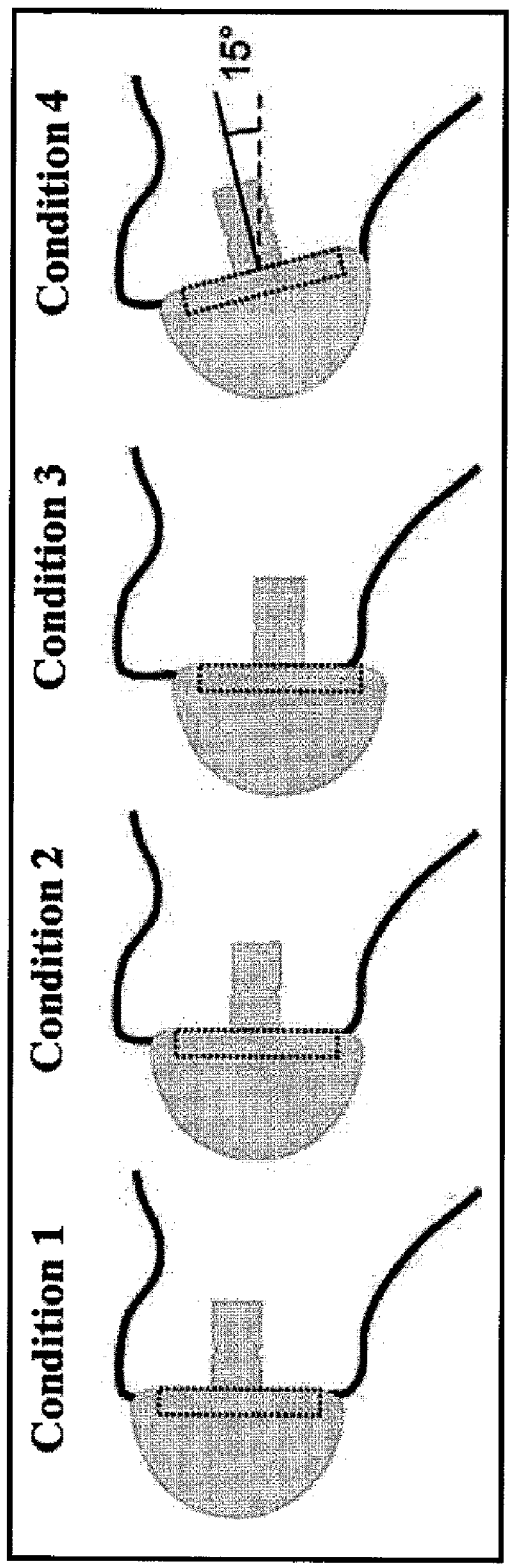
FIG. 27 shows conditions discussed in a study by Nyffeler.

To reduce the incidence of impingement and scapular notching, the neck angle of the reverse shoulder component may be reduced from 155° (the neck angle of the traditional Grammont reverse prosthesis and essentially every subsequent reverse shoulder prosthesis on the market) to 145°. Testing has demonstrated (see FIG. 26) that a 10° reduction in neck angle results in a downward shift in range of motion (ROM) . . . this downward shift acts to provide a ROM that is more in alignment with a patient's activities of daily living (ADL). Evidence of the need for a downward shift in ROM was objectively demonstrated in a study by De Wilde (see De Wilde, L. et al. Shoulder Prosthesis Treating Cuff Tear Arthropathy: a comparative biomechanical study. JOR 22: 1222-1230. 2004) who used radiographic templates to demonstrate that the traditional Grammont design was associated with inferior impingement at 16° abduction. Additional evidence of this design flaw is documented in a study by Nyffeler (see Nyffeler, R. et al. Biomechanical Relevance of Glenoid Component Positioning in the Reverse Delta III Total Shoulder Prosthesis. JSES. Vol. 14, #5: 524-528. 2005) who compared the incidence of scapular notching at 4 different conditions: 1) when the glenosphere is centered on the glenoid; 2) when the glenoid is positioned at the inferior glenoid rim; 3) when the glenosphere inferiorly overhangs by 2-4 mm; and 4) when the glenosphere is tilted inferiorly at 15 degrees and flush with the scapular neck; as depicted in FIG. 27. Nyffeler concluded that a glenosphere with an inferior overhang of 2-4 mm was associated with significantly improved abduction/adduction ROM (as a result of the reduced inferior impingement).

It should be noted that glenosphere conditions 2-4 in the Nyffeler study are believed to be surgical modifications to the manufacturer-endorsed technique [condition 1]—these modifications are believed to be necessary to specifically address the aforementioned design flaw. There may be some benefit to positioning the glenosphere so that it overhangs inferiorly; however, it is believed that locating the glenosphere inferiorly may present a number of new concerns— most notably in the presence of a central bone defect, as would be common in the conversion of a total shoulder to a reverse shoulder (to obtain inferior glenosphere overhang with typical reverse designs a hole would need to be drilled in the inferior portion of the glenoid, causing the removal of additional glenoid bone). In order to conserve this much needed glenoid bone, one embodiment of the present invention utilizes a glenoid plate so that its central stem is shifted superiorly by 4 mm—enabling the surgeon to maintain the traditional surgical technique with the reverse as would be performed for total shoulder arthroplasty (i.e. drilling a hole in the center of the glenoid where the defect would occur; thereby, conserving bone). From a technique standpoint, a hole is drilled in the center of the glenoid, the glenoid bone is reamed, and the glenoid plate is inserted and secured with screws so that the inferior edge of the plate would sit flush on the inferior edge of the native glenoid bone. An added advantage of the superiorly shifted stem is that the locking screw hole in the glenosphere will no longer be positioned at the apex of the glenosphere (a region which is commonly loaded)—instead it will be superiorly shifted to a region that is not as commonly loaded (which corresponds to the location of the superiorly shifted stem on the glenoid plate).

To improve stability and decrease the incidence of dislocation, the humeral liner may in one embodiment be brought out of the proximal humerus so that the proximal humerus is no longer used to establish the size of glenosphere. This feature may be advantageous for a number of reasons (including, bit not limited to): 1) proximal humeral bone is conserved since proximal reaming is not required and 2) the glenosphere size can be established by the size of the native glenoid bone (rather than being established by the size of liner placed in the proximal humerus)-testing has demonstrated improved ROM and stability with an increasing glenosphere diameter. This feature also facilitates the conversion from a hemi- or total shoulder to a reverse (or vice-versa: the conversion of a reverse to a hemi- or total shoulder) since this reverses design may utilize the same humeral stem as that used for hemi- and total shoulder arthroplasty (i.e. the surgeon does not have to remove a well fixed humeral stem to convert to a reverse shoulder). It should be noted that this embodiment maintains the same humeral neck cut that is utilized for a hemi- and/or total shoulder (i.e. the humeral head is resected at or about the anatomic neck). Other systems typically require a resection at a different location as that utilized for hemi- and/or total shoulder arthroplasty.

An additional embodiment to reduce the incidence of dislocation involves the use of a tension band that may connect the glenosphere and humeral components and may be sized according the length of the patient's deltoid. The band may break during trial reduction at a tension that corresponds to an appropriate lengthening of the deltoid to achieve adequate stability and function. Two studies by De Wilde (see De Wilde, L. et al. Shoulder Prosthesis Treating Cuff Tear Arthropathy: a comparative biomechanical study. OR 22: 1222-1230. 2004; De Wilde, L. et al. Functional Recovery after a Reverse Prosthesis for Reconstruction of the Proximal Humerus in Tumor Surgery. CORR. #430: 156-162. 2005) suggest that a 10-20% increase in deltoid length is appropriate.

In one example, the glenosphere and humeral size range is therefore increased to 38-46 mm (relative to the size range provided by competitive designs: 34-42 mm, which do not utilize this technique). To achieve these large size glenospheres the anterior and posterior sides of the glenospheres may be chamfered; thereby, allowing them to be inserted into the wound site and sit flush on the resected surface without having to remove any excess glenoid bone. The internal geometry of each glenosphere may be hollowed out to reduce its weight, doing so may minimize the incidence of fatigue-induced bone fractures. To increase ROM and improve stability, each glenosphere may have an extended articular surface (i.e. an arc larger than 180°—see FIG. 32).

To improve glenoid fixation, the invention may utilize a bone "through-growth" glenoid plate stem which accepts the use of bone graft. Bone graft can be placed into the stem prior to securing the plate with screws and/or after (e.g., by injecting the graft through a syringe in the top of the plate). The bone through-growth fixation stem can be either cylindrical (e.g., to revise a peg glenoid) or non-cylindrical (e.g., to revise a keel glenoid). Modifying the shape and profile of the glenoid plate may also improve glenoid fixation; in one example the inventors modified the plate from the traditional Grammont-style circular design (utilized by other conventional designs on the market) to a pear/oval design (which more accurately reflects the anatomy of the scapula). Doing so may improve glenoid fixation by allowing for an increase in the number of glenoid screw holes available for fixation (e.g., an increase from 4 to 6) and an improvement in the position of the screw holes so that it maximizes the potential for fixation (i.e. each screw hole is located according the region of best quality/deepest bone). FIGS. 12-15 further elaborate on these advantages. More particularly: FIG. 12 summarizes the results of two different anatomic studies (Iannotti, J. P. et al. The Normal Glenohumeral Relationships. JBJS. Vol. 74-A, #4: 491-500. 1992; Checroun, A. J. et al. Fit of Current Glenoid Component Designs: an Anatomic Cadaver Study. JSES. Vol. 11, #6: 614-617. 2002); each of these studies demonstrate that the glenoid is wider inferiorly than superiorly and that it has a characteristic pear or "inverted-comma" shape. FIG. 13 graphically illustrates the fit of a typical Grammont-style glenoid plate on a representative glenoid fossa; it is believed that the typical 4-quadrant location of the screw holes is not ideal due to the anterior and posterior slope of the scapula—this slope results in a thin base of bone in these locations. FIG. 14 graphically illustrates the region of best quality/deepest bone in the native glenoid. Finally, FIG. 15 graphically illustrates the rationale for screw hole position utilized in an embodiment of the present invention.

The glenoid plate may also incorporate several other features which should work to conserve glenoid bone and/or improve fixation. The glenoid plate may have a curved-back to minimize the amount of bone removed for implantation, (compared to the flat-back glenoid plate designs, as the native glenoid bone is also curved). Additionally, one or more screw holes in the glenoid plate may have a female spherical feature which mates with the male spherical head of the compression screw. Doing so may allow for each compression screw to be angled/oriented in any desired direction—thereby improving the possibility of screw purchase. Additionally, one or more of the screw holes in the glenoid plate may have a threaded feature for attachment of a locking cap—this cap screw may have a female spherical feature which compresses the spherical head of the compression screw; thereby locking it to the plate at whatever angle/orientation the screw was inserted into the bone (preventing it from backing out).

Various details of a reverse shoulder design according to an embodiment of the present invention are shown herein. FIGS. 16A-16D depict the assembled construct of an example reverse shoulder prosthesis. The components of this construct include a humeral stem (which may be used in pressfit and/or cemented applications and may be constructed from titanium), a humeral liner (a concave component which mates with the convex glenosphere; may be constructed from UHMWPE), a humeral adapter plate (which connects the humeral liner to the humeral stem; may be constructed from titanium), a glenosphere (may be constructed from cobalt chrome), a glenoid plate (may be constructed from titanium), and a number of screws and fixations devices for assembly of the individual components to one another and for assembly of the construct to the native bone (all may be constructed from titanium). FIGS. 17A-17D depict an example glenoid plate design (several features should be noted: 1) the 6 screw holes on the backside of the plate, and 2) the bone "through-growth" cage stem which enables bone graft to be injected via syringe through the front of the plate and/or placed through the hole in the bottom surface of the cage stem). FIGS. 18A-18D and 5D-5F depict two other embodiments of the glenoid plate design (incorporating curved back glenoid plates). FIG. 25 depicts an example compression screw (note the spherical head which enables the screw to be angularly oriented in any desired direction).

As discussed above, varies embodiments of the reverse shoulder design may include (but not be limited to): Superiorly shifted Glenoid Plate Stem; Non Cylindrical Glenoid Plate Stem; Oval/Pear Shaped Glenoid Plate to Improve Fixation; Non 155 Degree Humeral Neck Angle; Extended Articular Surface Glenosphere; and/or Tension Band to gage deltoid tension; a bone "through growth" cage may be applied for use in the reverse shoulder prosthesis.

Figure 28:
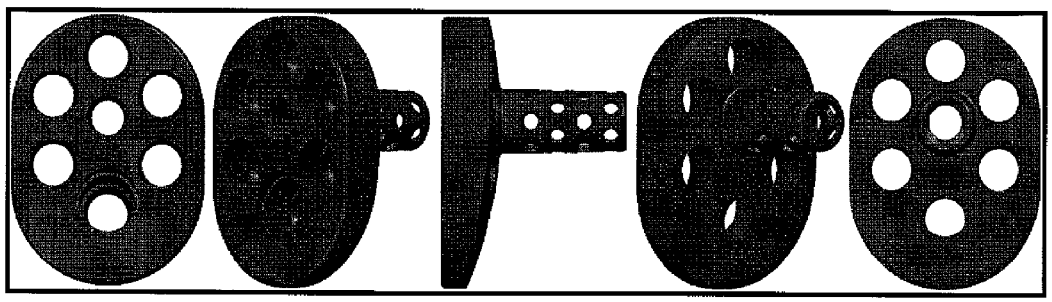
FIG. 28 shows a number of views of a glenoid plate according to another embodiment of the present invention.
Figure 29:
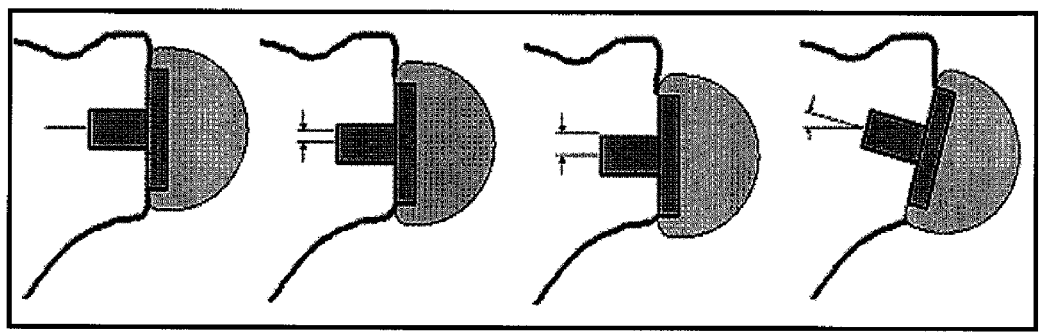
FIG. 29 shows a modified image from Nyffeler study in which the clinical effectiveness of 4 different Glenosphere positions were examined.

As described herein, one embodiment of the present invention relates to a superiorly shifted glenoid plate stem (see, e.g., FIG. 28 as well as other Figs. herein). In this regard, an inferiorly overhanging glenosphere is associated with less scapular notching and a better clinical result (based upon the clinical observations by Nyffeler—third image from left in FIG. 29 (modified image from Nyffeler study in which the clinical effectiveness of 4 different Glenosphere positions were examined)). However, the positioning the glenosphere inferiorly may present a number of new concerns, mainly, in the presence of a central bone defect as would be common in the conversion of a total shoulder to a reverse shoulder (as a result of the glenoid being removed). To obtain inferior glenosphere overhang with other reverse designs, a hole would typically need to be drilled in the inferior portion of the glenoid, causing the removal of additional glenoid bone. In order to conserve this much needed glenoid bone, a glenoid plate according to one embodiment is designed so that its central stem is shifted superiorly (e.g., by 4 mm)—enabling the surgeon to maintain the traditional surgical technique with the reverse as would be performed for total shoulder arthroplasty (i.e. drilling a hole in the center of the glenoid where the defect would occur; thereby, conserving bone). Additionally, with other glenoid plate designs the inferior hole (which is typically angled inferiorly to allow for insertion of a screw along the inferior scapular neck) is typically no longer in the correct position to allow the screw to be inserted along the inferior scapular neck.

Figures 30A, 30B:
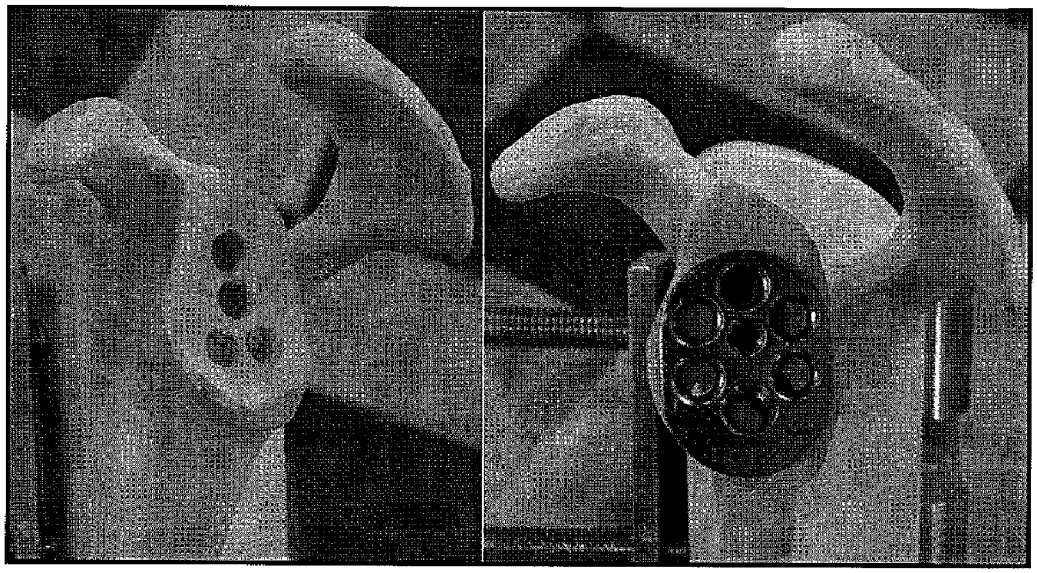
FIGS. 30A and 30B show another embodiment of the present invention related to glenoid plate hole positions that are designed to allow conversion or revision of a traditional pegged glenoid.
Figures 31A, 31B:
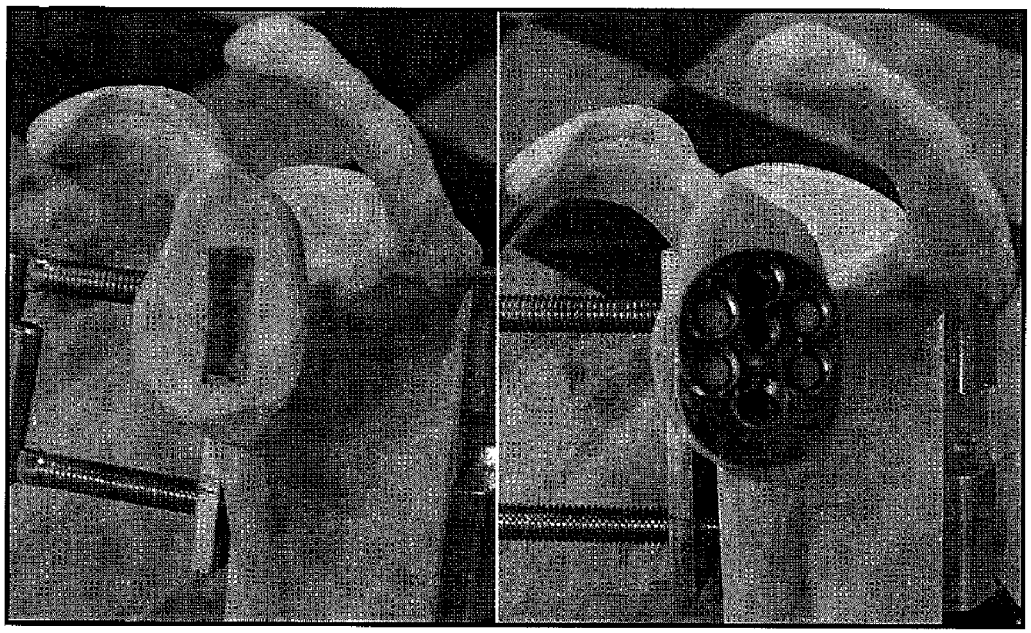
FIGS. 31A and 31B show another embodiment of the present invention related to glenoid plate hole positions that are designed to allow conversion or revision of a traditional keeled glenoid.

As further described herein, another embodiment of the present invention relates to glenoid plate hole positions that are designed to allow conversion of a traditional peg and keel glenoid. In the case of the revised peg glenoid, the central peg of the glenoid plate of this embodiment is designed to fill the central bone defect left by the removed glenoid's central peg. As depicted in FIGS. 30A and 30B, the superior anterior/posterior set of screw holes are positioned at a location where no bone was removed in the revision of a pegged glenoid; using these features, adequate fixation was achieved. The tilted inferior hole and superior hole also successfully contributed to fixation, particularly when the ±10° angulation of the compression screws were utilized. In the case of the revised keeled glenoid, the central stem of the glenoid plate of this embodiment is designed to partial fill the central bone defect left by the removed keeled glenoid; graft may be used to completely fill the defect—which could be, for example, injected in the front (see below for additional discussion). As depicted in FIGS. 31A and 31B, the two sets of anterior/posterior holes are positioned at a location where no bone was removed in the revision of the keeled glenoid; using these features, adequate fixation was achieved. As in the revision of a pegged glenoid, the tilted inferior hole and superior hole also successfully contributed to fixation, particularly when the ±10° angulation of the compression screws were utilized.

Figure 32:
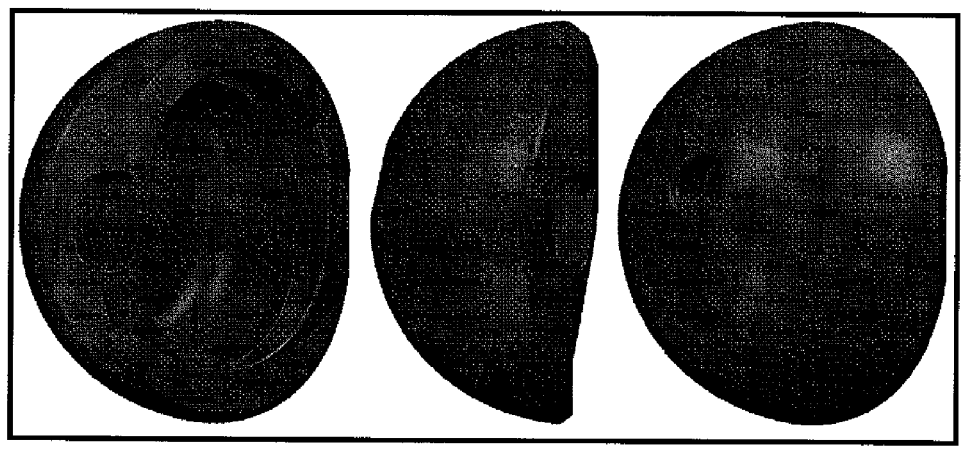
FIG. 32 shows another embodiment of the present invention related to anterior/posterior glenosphere flats.

As further described herein, another embodiment of the present invention relates to anterior/posterior glenosphere flats (see, e.g., FIG. 32 as well as other Figs. herein).

As further described herein, another embodiment of the present invention relates to an extended articular surface to improve ROM (i.e. greater than 180 degrees articular surface—see, e.g., FIG. 32 as well as other Figs. herein).

To improve stability and decrease the incidence of dislocation, the humeral liner of this embodiment was brought out of the proximal humerus (as is the case in the traditional Grammont design) so that the proximal humerus is no longer used to establish the size of glenosphere. This feature is advantageous for a number of reasons: 1) proximal humeral bone is conserved, since proximal reaming is not required and 2) glenosphere size can be established based upon the size of the native glenoid bone (rather than being established by the size of liner placed in the proximal humerus). Testing has demonstrated that improved ROM and stability can be achieved with a larger glenosphere diameter of this embodiment. This feature also better facilitates the conversion from a hemi- or total shoulder to a reverse (or vice-versa: the conversion of a reverse to a hemi- or total shoulder), because the reverse design of this embodiment utilizes the same humeral stem as that used for hemi- and total shoulder arthroplasty (i.e. the surgeon does not have to remove a well fixed humeral stem to convert to a reverse shoulder). It should be noted that this embodiment also maintains the same humeral neck cut that is utilized for a hemi- and/or total shoulder (i.e. the humeral head is resected at or about the anatomic neck). Other systems typically require a resection at a different location as that utilized for hemi- and/or total shoulder arthroplasty. Therefore, the glenosphere and humeral liner size range in this embodiment is increased to 38-46 mm (relative to the size range provided by the other designs on the market of 34-42 mm, which do not utilize this technique). To achieve these large glenosphere sizes, the anterior and posterior sides of the glenospheres may be chamfered. This allows the glenosphere to be inserted into the wound site and sit flush on the resected surface without having to remove any excess glenoid bone. In certain conventional systems the glenosphere is spherical, by chamfering the anterior and posterior sides of the glenosphere the inventors are able to make the shape of the glenosphere better resemble that of the native glenoid which is thinner in the anterior and posterior directions. Additionally, adding an anterior and posterior chamfer to the glenosphere under this embodiment has the added benefit of making it easier to insert since it allows it to more easily get by the humerus during insertion of the device.

Regarding other features of the glenosphere under various embodiments of the present invention, the internal geometry of each glenosphere may be hollowed out to reduce its weight (and provide space for a locking cap). This may minimize the incidence of fatigue-induced bone fractures. Additionally, to increase ROM and improve stability, each glenosphere may have an extended articular surface (i.e. an arc larger than 180 degrees—see FIG. 32).

In another embodiment of the present invention an optimized combination of humeral neck angle, humeral liner constraint, glenosphere diameter, and glenosphere thickness may be used to maximize ROM and jump distance and limit scapular notching.

Figure 33:
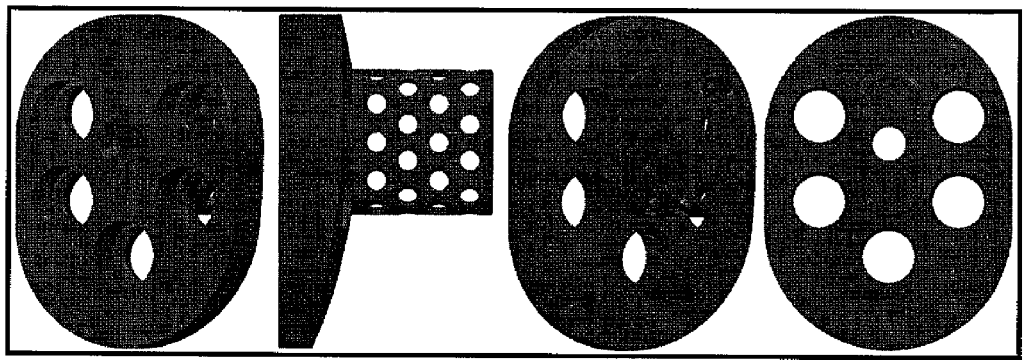
FIG. 33 shows another embodiment of the present invention related to a bone cage.

In another embodiment of the present invention a bone cage (cylindrical and/or noncylindrical—for example, to fill a bone defect in the revision of a pegged and/or keeled glenoid—see, e.g., FIGS. 28 and 33, respectively) with a frontal opening to allow bone through growth and insertion of a therapeutic agent before and/or after implantation in situ and/or through the front in a revision case may be provided.

In another embodiment, a method of reconstructing a diseased shoulder is provided, comprising: providing a glenosphere, a glenoid plate and a humeral liner which interact to achieve a range of motion of a desired number of degrees (e.g., in at least a generally superior-inferior direction).

As discussed herein, various embodiments of the present invention provide an anatomic design of a glenoid plate which enhances stress transfer to the glenoid fossa and limits prosthesis A/P overhang. Additionally, the anatomic shaped glenoid plate may optimize the number of screw holes that can be used for fixation while at the same time maximizing their location relative to the best quality/deepest bone available in the native glenoid. Moreover, one or more compression screws may be utilized as locking screws by using a locking cap screw.

Reference will now be made to a study to evaluate the relationships between the design parameters associated with the typical Grammont reverse shoulder design and the commonly reported clinical complications. The results of this study may be used to identify and establish design inputs used for a reverse shoulder prosthesis according to various embodiments of the present invention.

Figure 34:
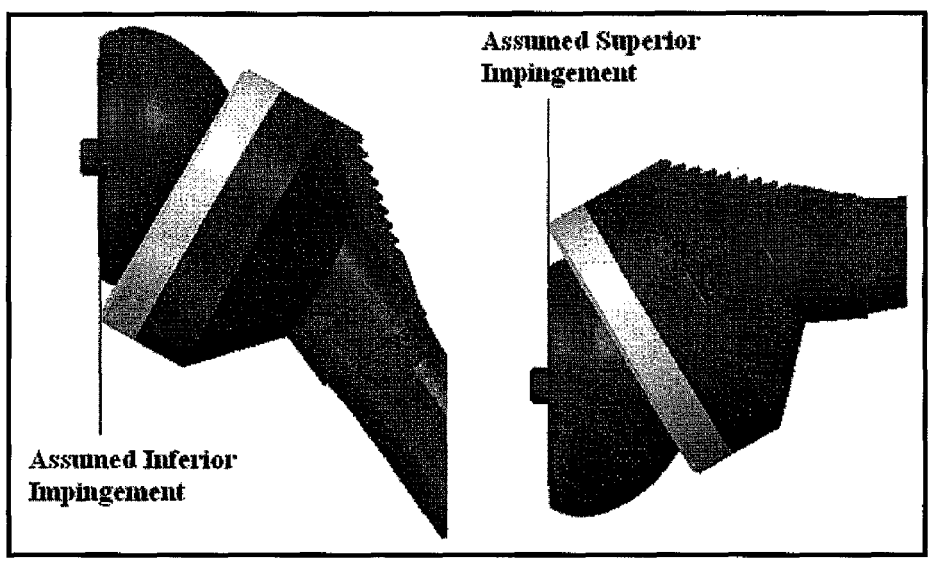
FIG. 34 shows a diagram associated with the definition of inferior and superior impingement.
Figure 35:
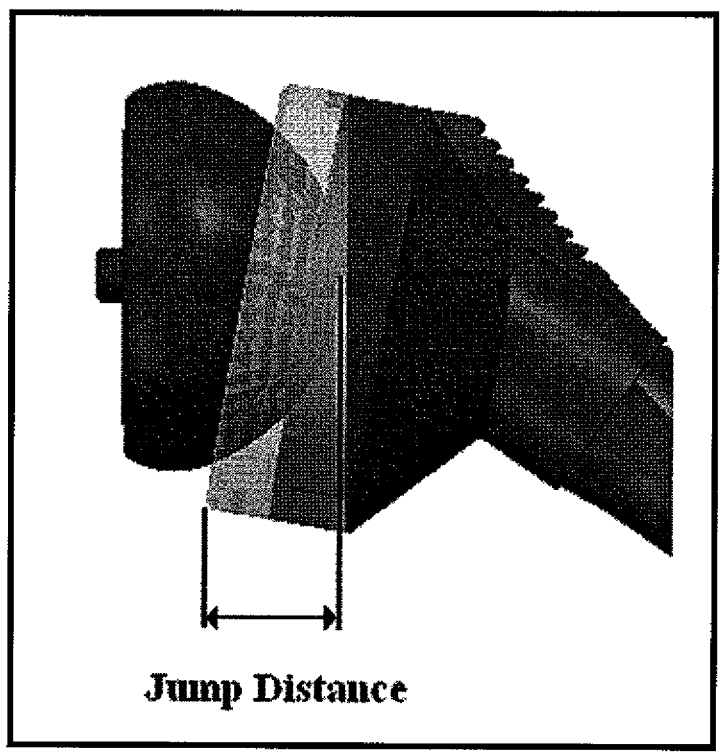
FIG. 35 shows a diagram associated with the definition of jump distance.
Figure 36:
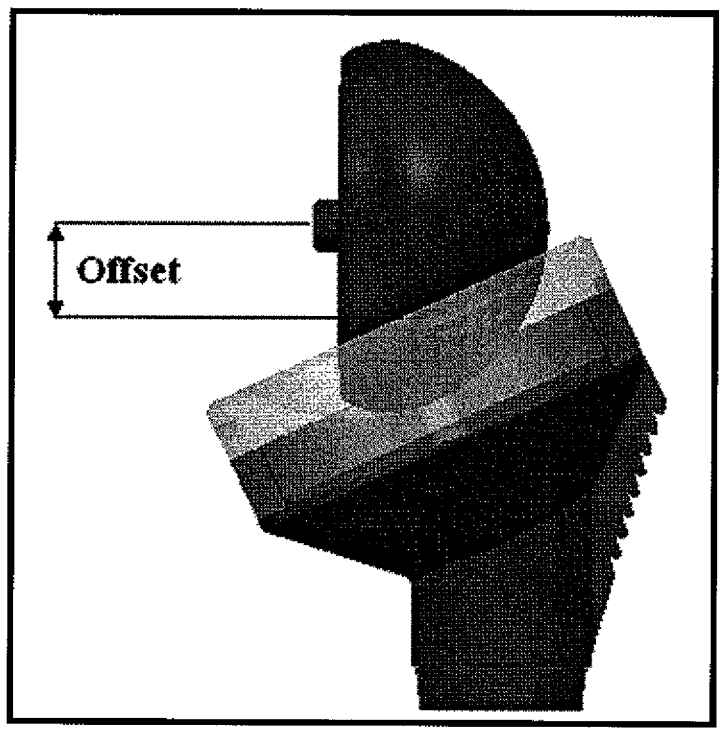
FIG. 36 shows a diagram associated with the definition of offset.
Figure 37:
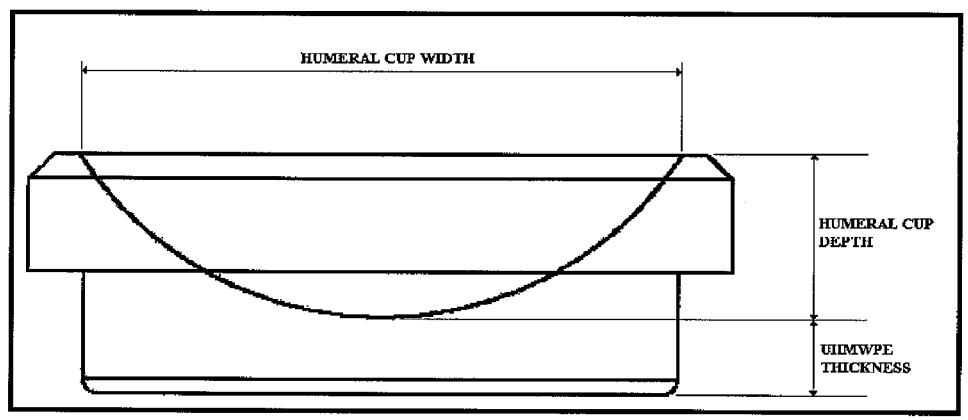
FIG. 37 shows a diagram associated with the definition of humeral constraint.

For the purposes of this discussion, the following definitions may apply: Range of Motion (ROM) is defined as the humeral rotation occurring between inferior and superior impingement, wherein inferior and superior impingement are defined as the point where the liner extends past the glenosphere (see FIG. 34). It should be noted that rotation of the scapula was not considered in this measurement; only humeral motion was considered to enable a one-to-one comparison between designs. Therefore, the presented ROM values are not intended to correspond with clinically reported values. Jump Distance is defined as the lateral distance necessary for the glenosphere to escape from the humeral liner; it is a measure of the resistance to dislocation (assuming no impingement) (see FIG. 35). Offset is defined as the vertical distance between the center of the humeral liner and glenosphere; it is related to deltoid tensioning (see FIG. 36). Humeral Constraint is defined as the ratio between humeral liner depth and width (at its face). For clarification, a constraint >0.5 is a constrained joint (see FIG. 37).

Under the study, a typical 36 mm Grammont reverse shoulder prosthesis (Depuy, Inc./Tornier Inc.) was obtained and reverse engineered using an optical comparator and calipers. The prosthesis was then geometrically modeled (in a parametric fashion—thereby allowing the design parameters to be varied) using Unigraphics (UGS, Inc.) based upon the elucidated design parameters. A ROM simulation was constructed (also using Unigraphics) to simulate humeral abduction/adduction and quantify the aforementioned study parameters.

The subject typical Grammont reverse shoulder was geometrically modeled using three dimensional (3-D) computer-aided design software (Unigraphics; UGS, Inc.). An assembly analysis was conducted to quantify the effect of several prosthetic design parameters (humeral neck angle, humeral liner constraint, glenosphere thickness, and glenosphere diameter) on several functionally relevant measurements (ROM, jump distance, and offset) during simulated humeral abduction/adduction. By implication, the relationship between the aforementioned design parameters and functional measurements will elucidate the failure mechanisms associated with the commonly reported clinical complications for reverse shoulder arthroplasty (scapular notching, dislocation, improper deltoid tensioning, etc. . . . ). Specifically, ROM, jump distance, and offset were quantified and compared for each of the following design conditions: as humeral neck angle varied from 130 to 165° (in 5° increments); as humeral constraint varied from 0.250 to 0.3125 (in 0.0125 increments); as glenosphere thickness varied from 17 to 21 mm (in 1 mm increments); and as glenosphere diameter varied from 34 to 44 mm (in 2 mm increments).

Figure 38:
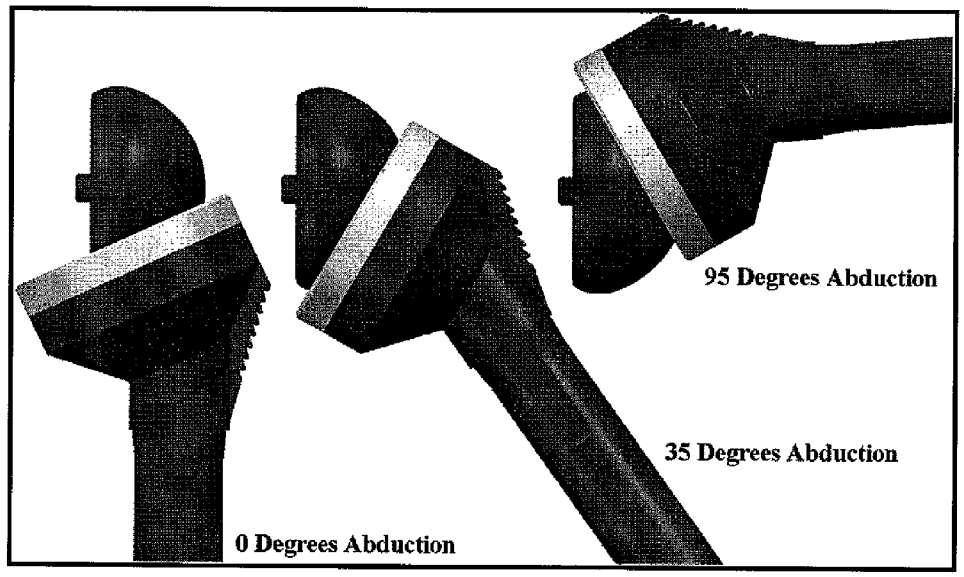
FIG. 38 shows a diagram associated with a typical Grammont reverse shoulder ROM.

Under this study the typical Grammont reverse shoulder (i.e. 155° neck angle, humeral constraint of 0.275, 36×19 mm Glenosphere) was observed to impinge inferiorly and superiorly at 35° and 95° abduction, respectively. (see FIG. 38).

Figure 39:
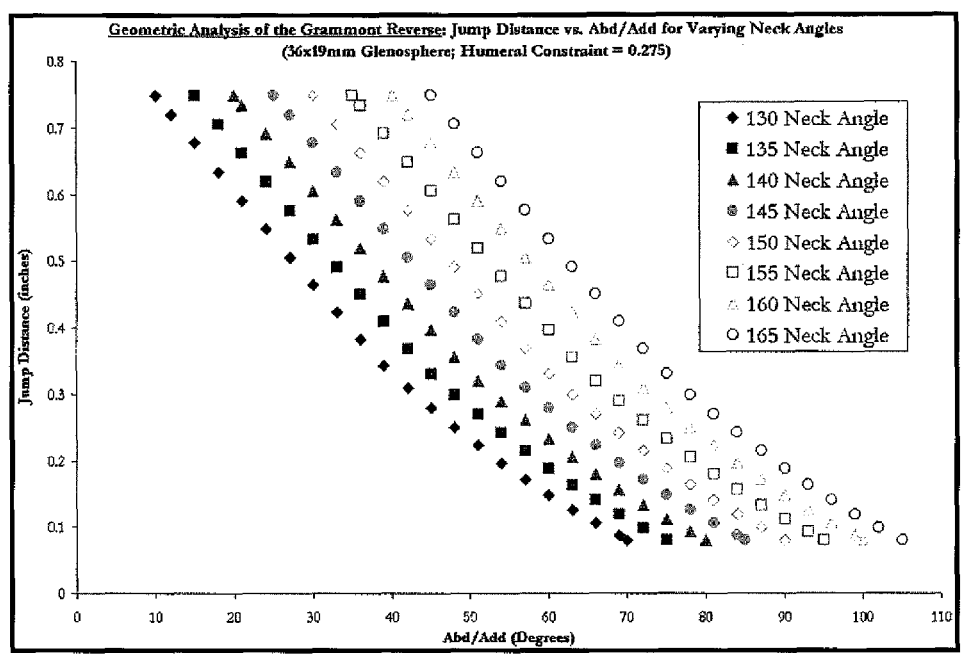
FIG. 39 shows a graph of effect of humeral neck angle on ROM and jump distance.

Increasing the humeral neck angle by 5° positively shifts the ROM by 5° by changing the points of impingement. Additionally, increasing the humeral neck angle by 5° also increases the offset from 0.25 to 0.5 mm, depending upon the angle of abduction. For clarification, the Nyffeler study reported that implanting a glenosphere with a 15° inferior tilt was associated with a decrease in scapular notching. FIGS. 39 and 40 illustrate why—removing 15° from the glenosphere is functionally the same thing as removing 15° from the humeral neck angle. Both minimize inferior impingement; the only difference being in the later, glenoid bone is conserved.

Increasing the humeral constraint by 0.0125 decreases the ROM by 4°; more constraint, less motion (see FIG. 41). Similarly, increasing the humeral constraint by the same amount also increases the jump distance by 0.5 mm; more constraint, greater resistance to dislocation.

Increasing glenosphere thickness by 1 mm (when humeral constraint is constant) increases the ROM by 5°. Offset and Jump Distance are not affected (see FIG. 42).

Increasing glenosphere diameter by 2 mm (when humeral constraint is constant) increases the jump distance by 0.5 mm. ROM is not affected (see FIG. 43).

Figure 44:
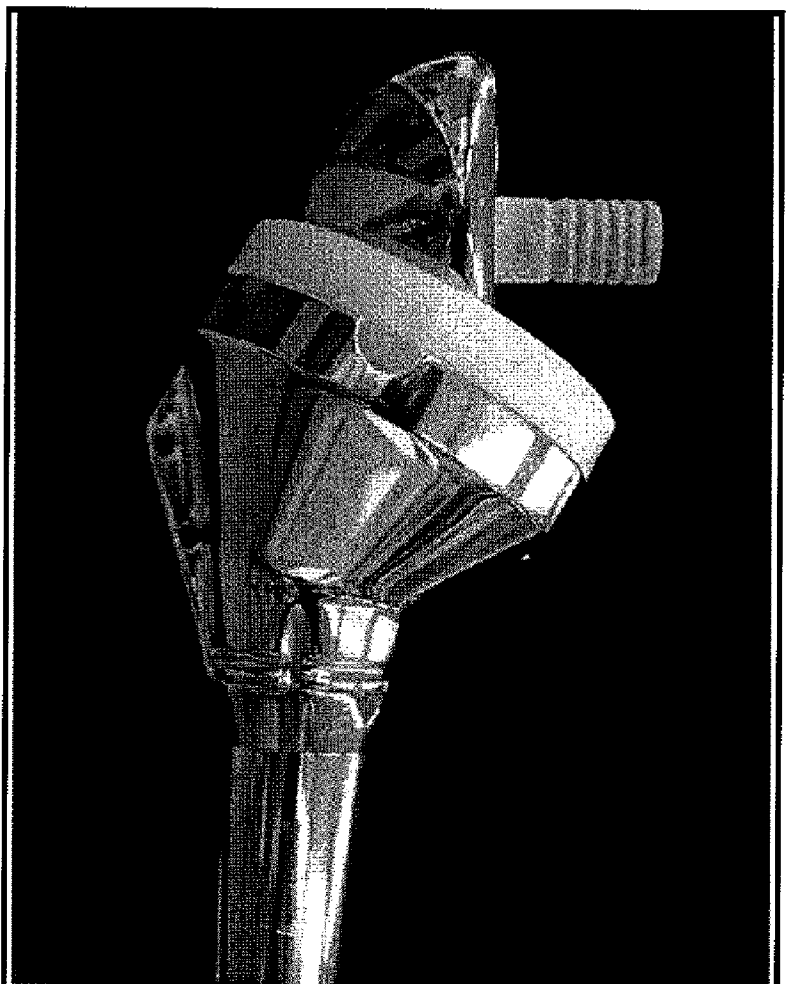
FIG. 44 shows an image from the Nyffeler study depicting the degree of inferior impingement when the humeral stem is placed in neutral position.

The results of this study demonstrate the relationship between each design parameter and functional measurement. Furthermore, the results demonstrate the typical Grammont design inferiorly impinges on the scapula prior to the patient being able to adduct his/her arm to their side, which is required for many activities of daily living. These results are validated by those presented in the literature from both radiographic and clinical studies (see FIG. 44; see also, Nyffeler, R. W. et al. Biomechanical Relevance of Glenoid Component Positioning in the Reverse Delta III Total Shoulder Prosthesis. JSES. Vol. 14. #5: 524-528. 2005; De Wilde, L. F. et al. Shoulder Prostheses Treating Cuff Tear Arthropathy: a comparative biomechanical study. JOR. #22: 1222-1230. 2004).

Based upon these observations, the conclusion is that the specific combination of humeral neck angle, glenosphere geometry, and humeral liner geometry are interrelated but not necessarily optimized in the traditional Grammont design—and thus make it susceptible to scapular notching and dislocation via inferior impingement. The knowledge of these relationships can serve as the basis for optimizing a traditional Grammont-style reverse shoulder prosthesis according to various embodiment of the present invention.

In this regard, various embodiments of the present invention may provide a reverse shoulder design shifting the inferior impingement point to a location that permits a ROM better accommodating a patient's activities of daily living. The application of these relationships is useful in the design of a reverse shoulder prosthesis that maximizes ROM and jump distance, minimizes impingement, and provides sufficient offset to tension the deltoid and maintain certain biomechanical benefits associated with the traditional Grammont reverse shoulder design.

Reference will now be made to another study to: 1) quantify the range of motion and jump distance associated with an Equinoxe reverse shoulder design during simulated humeral abduction/adduction as determined using a three-dimensional computer aided assembly analysis; and 2) compare these parameters to those associated with the typical Grammont reverse shoulder design during the same simulated motion, quantified using the same methodology. The results of the comparison verify that the Equinoxe reverse shoulder achieves an increase in the amount of motion and a decrease in the amount of inferior impingement (a measure of motion and stability, indicative of scapular notching) while maintaining a similar amount of jump distance (a measure of stability, indicative of the probability of dislocation), relative to the typical Grammont design.

The Equinoxe reverse shoulder that is the subject of this study was designed based upon the principles elucidated and described in connection with the study described above. Some design goals of this prosthesis are described below (some the design specifics of each component are shown in FIGS. 45-53):

1) Maintain the Biomechanical Benefits of the typical Grammont Reverse Design: Prevent Superior Humeral Migration, Minimize Lever Arm by Placing Center of Rotation on Glenoid Fossa (by moving it medially and distally), Elongate Deltoid by 15%.
2) Minimize Scapular Notching/Inferior Bone Impingement
3) Improve Range of Motion
4) Maximize Jump Distance
5) Seamlessly Integrate Equinoxe Primary System with a Reverse Option (i.e. utilize the same humeral stem)

As described below, this study demonstrates that the Equinoxe reverse shoulder achieves an increase in the amount of motion and a decrease in the amount of inferior impingement (a measure of motion and stability, indicative of scapular notching) while maintaining a similar amount of jump distance (a measure of stability, indicative of the probability of dislocation), relative to the typical 36 mm Grammont design.

For the purposes of this study, the aforementioned prostheses were designed and geometrically modeled by using Unigraphics (UGS, Inc.), based upon the elucidated design parameters described in the study discussed above. A ROM simulation was constructed (also using Unigraphics) to simulate humeral abduction/adduction and quantify the aforementioned study parameters.

Figure 45:
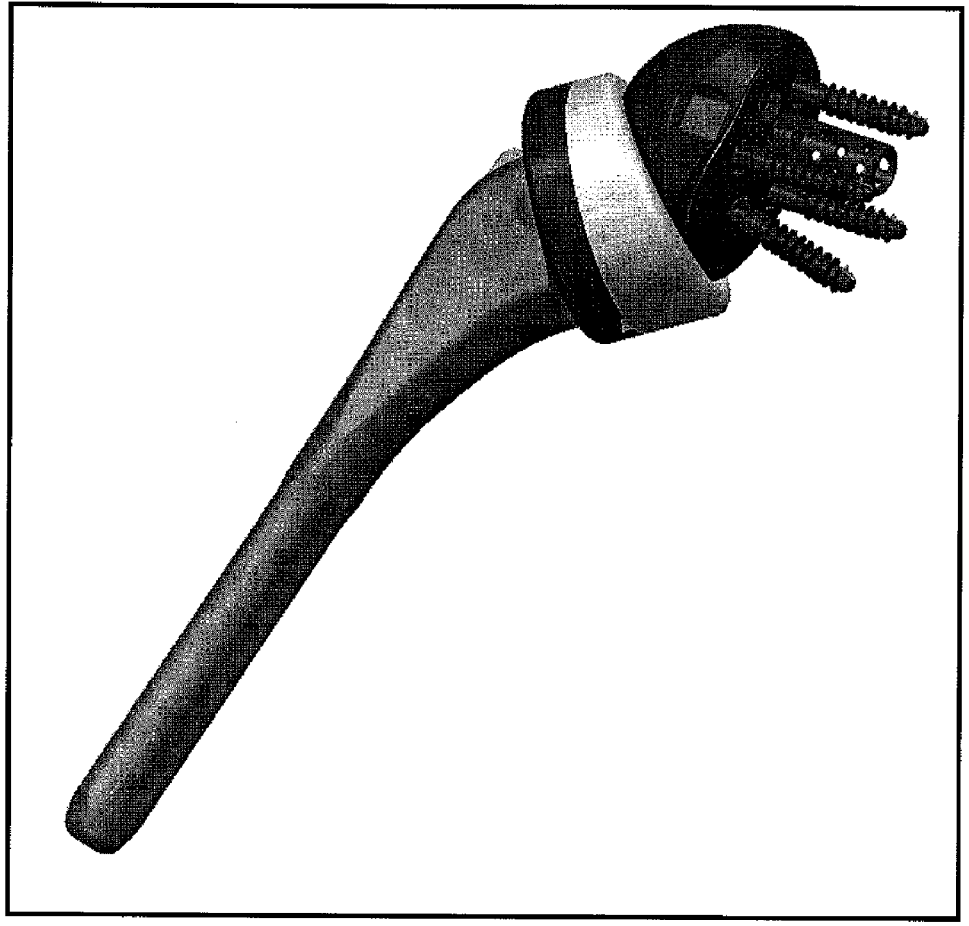
FIG. 45 shows another embodiment of a reverse shoulder prosthesis.
Figure 46:
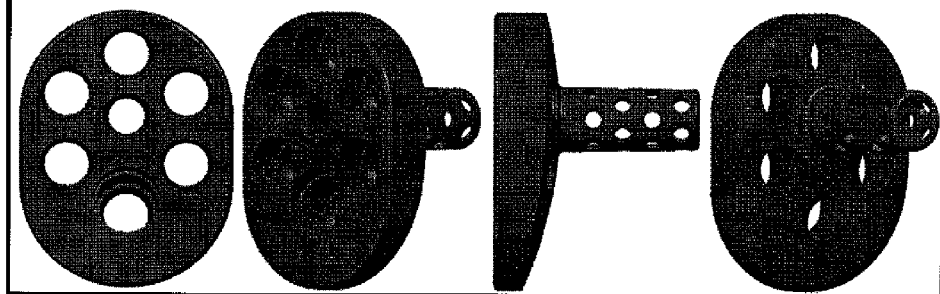
FIG. 46 shows another embodiment of a reverse glenoid plate design.
Figure 47:
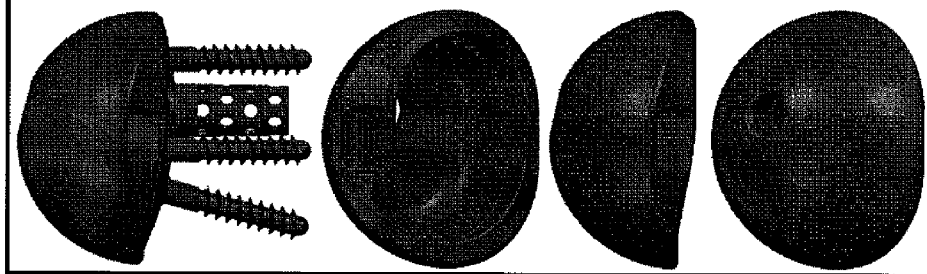
FIG. 47 shows another embodiment of a reverse glenosphere design.
Figure 48:
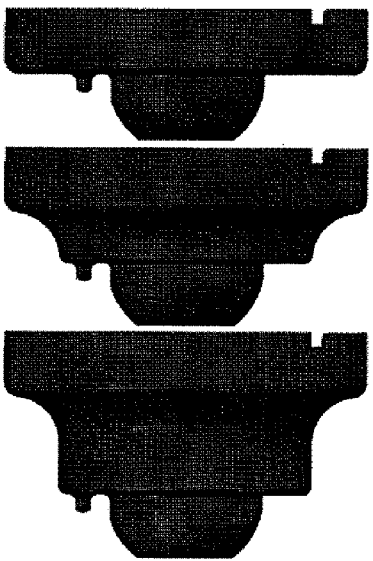
FIG. 48 shows other embodiments of a reverse humeral plate design.
Figure 48:
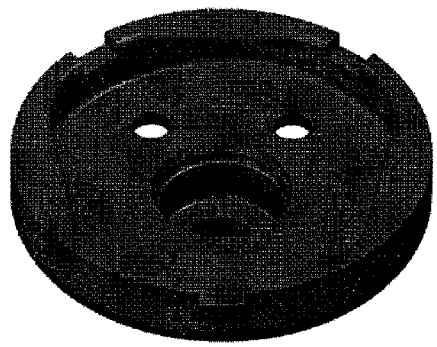
Figure 49:
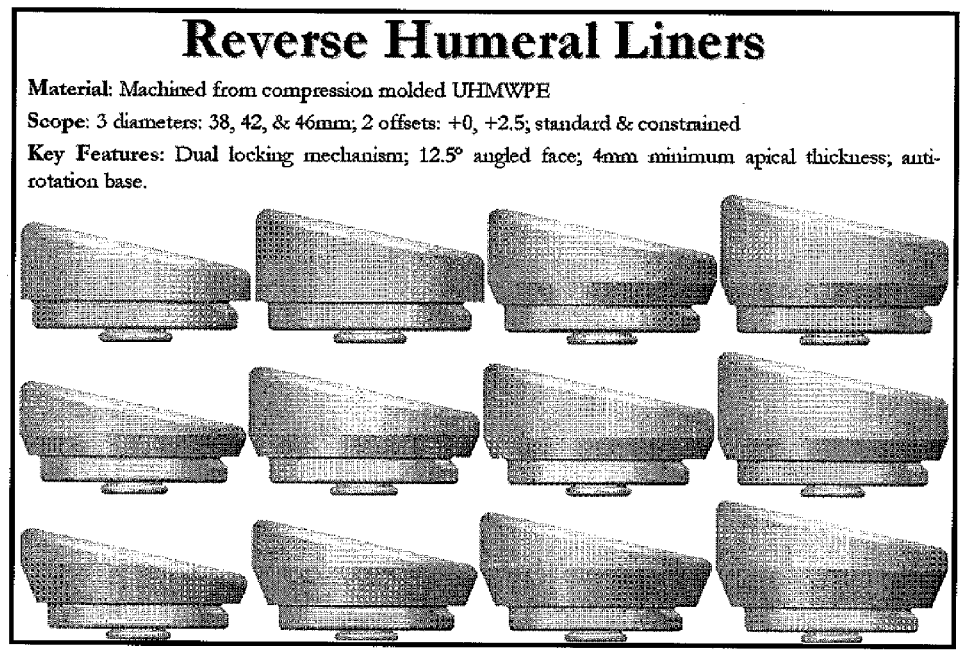
FIG. 49 shows other embodiments of a reverse humeral liner design.
Figure 50:
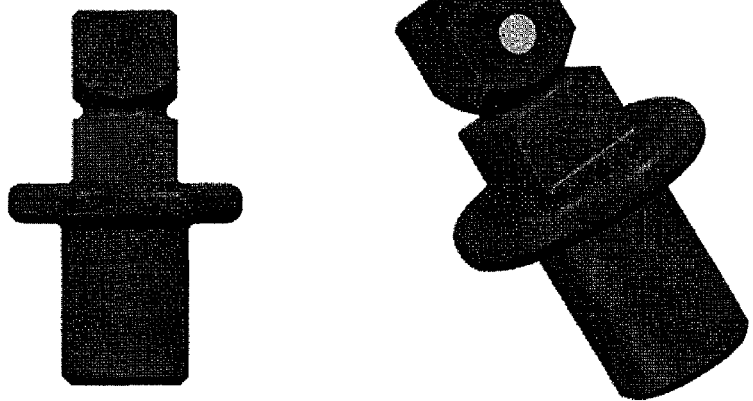
FIG. 50 shows another embodiment of a reverse torque defining screw driver design.
Figure 51:
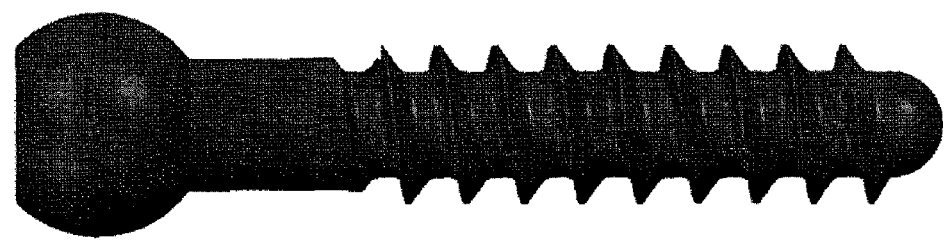
FIG. 51 shows another embodiment of a compression screw design.
Figure 52:
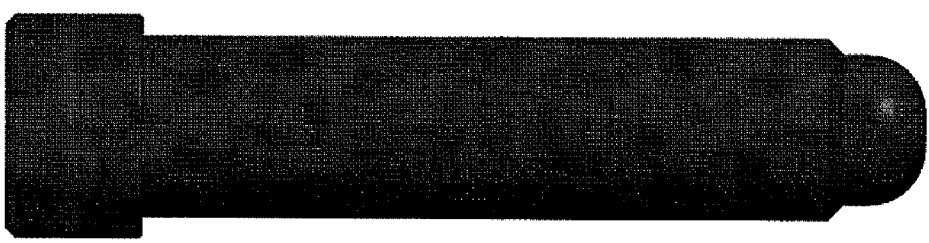
FIG. 52 shows another embodiment of a reverse glenosphere locking screw design (the threads are not shown in this view)
Figure 53:
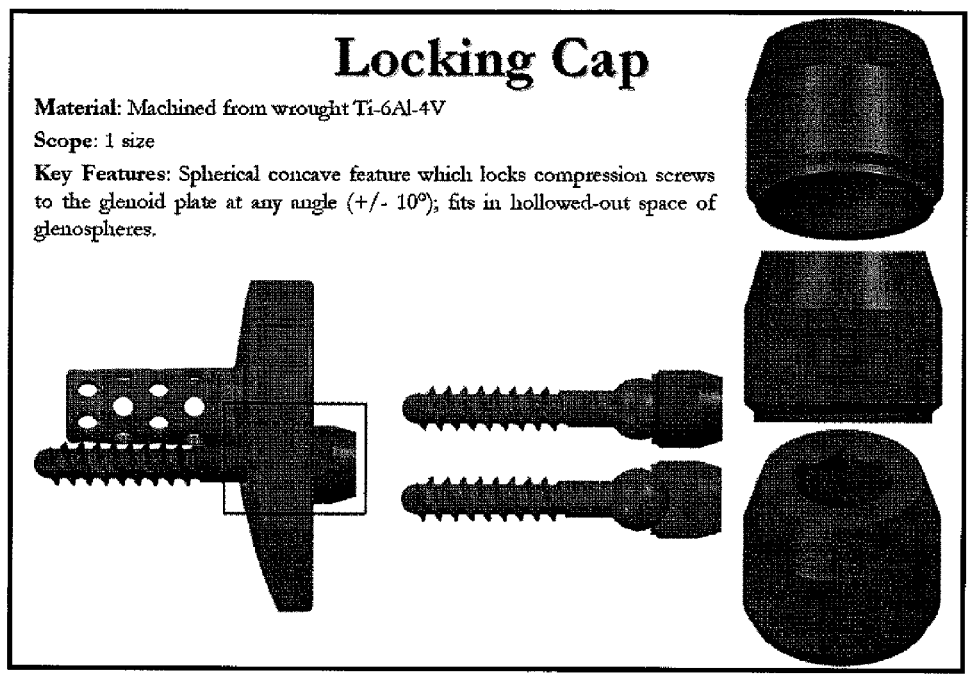
FIG. 53 shows another embodiment of a locking cap design.
Figure 54:
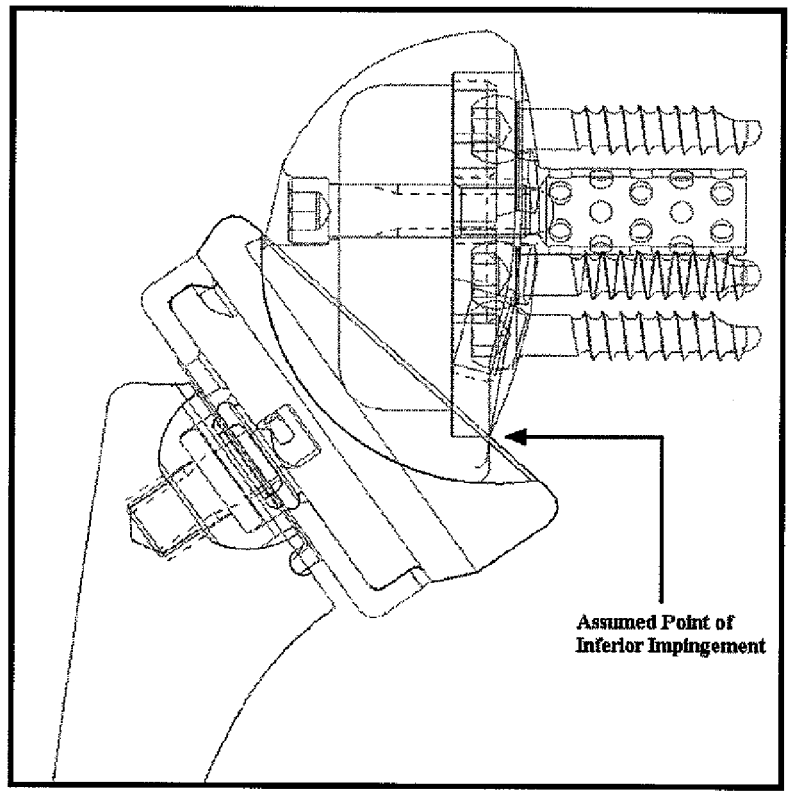
FIG. 54 shows a diagram associated with a defined point of inferior impingement.
Figure 55:
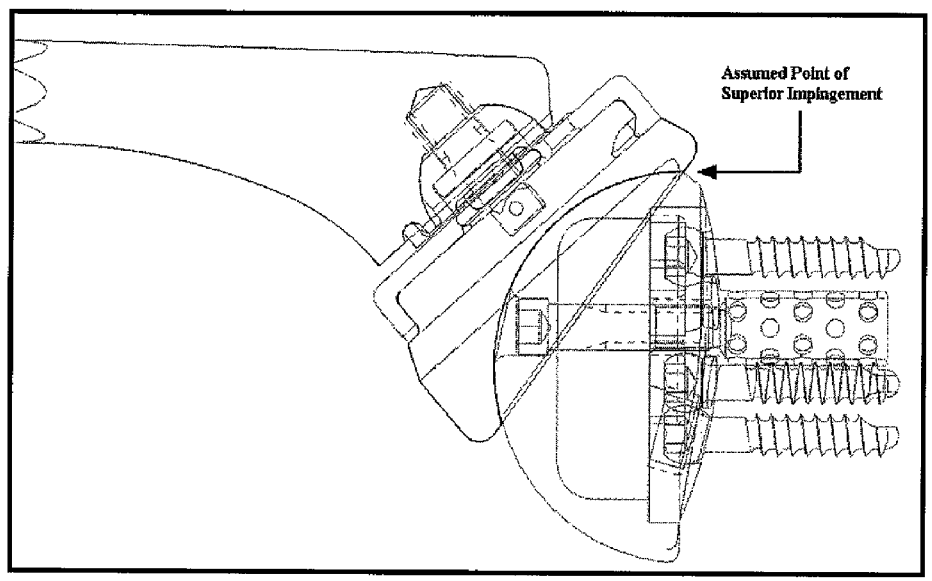
FIG. 55 shows a diagram associated with a defined point of superior impingement.

The same methodology described in the study discussed above was applied to quantify the points of inferior and superior impingement, the total ROM, and the jump distance at 3° increments during simulated humeral abduction/adduction of the Equinoxe reverse shoulder prosthesis. It should be noted that the definitions used in this study for inferior and superior impingement are slightly different than those used in the study discussed above due to the differences in design. As shown in FIGS. 45 and 46, the Equinoxe reverse shoulder glenoid plate has a central stem that is superiorly shifted by 4 mm; doing so, results in a 4 mm distal shift to the glenosphere assuming that the central stem of the glenoid plate is implanted so that the distal rim of the glenoid plate aligns with the distal edge of the glenoid articular surface. A 4 mm distal shift of the glenosphere creates an inferior overhang that has been demonstrated by Nyffeler to be associated with superior clinical results, compared to alternative glenosphere implantation techniques. For this reason the defined points of inferior and superior impingement are modified as depicted in FIGS. 54 and 55, respectively.

Figure 56:
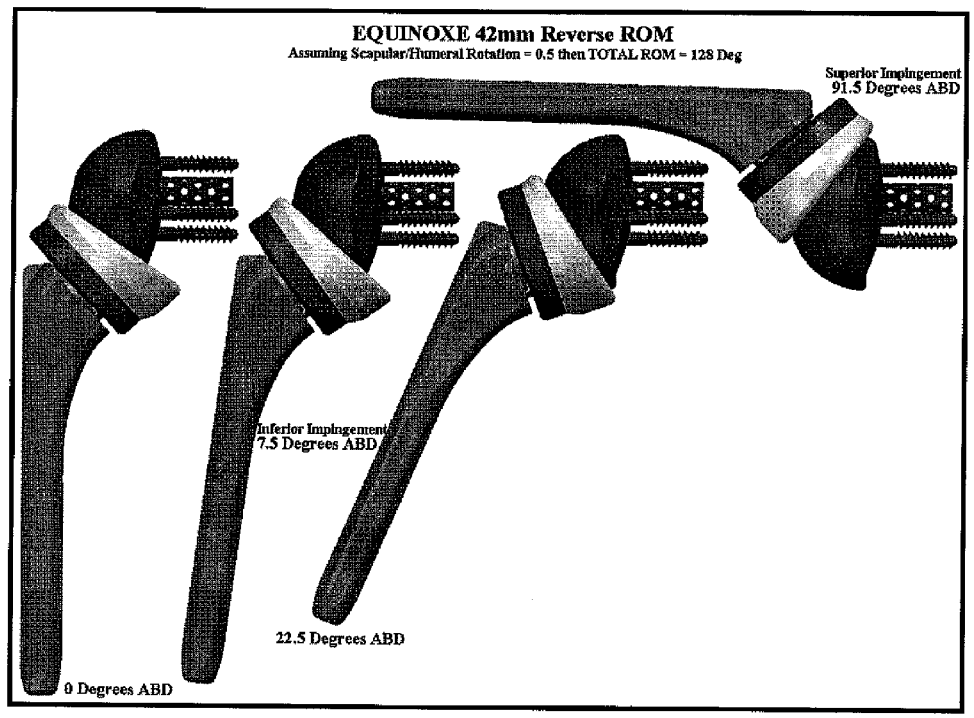
FIG. 56 shows ROM associated with another embodiments of a reverse shoulder prosthesis.

During simulated humeral abduction/adduction, inferior and superior impingement was measured to occur for the 38 mm, 42 mm, and 46 mm Equinoxe reverse shoulder at 16° and 91.5°; 7.5° and 91.5°; and 0° and 91.5°, respectively. Therefore, the total ROM during simulated humeral abduction/adduction for the 38 mm, 42 mm, and 46 mm Equinoxe reverse shoulder was measured to be 75.5°, 84°, 91.5°, respectively. For clarification, FIG. 56 depicts several defined angles during this simulated motion for the 42 mm Equinoxe reverse shoulder of this example.

Over this ROM, the minimum and maximum jump distance associated with the 38 mm, 42 mm, and 46 mm Equinoxe reverse shoulder was measured to be 0.035 in-0.855 in; 0.035 in-1.052 in; and 0.035 in-1.234 in, respectively. The average jump distance (in 3° increments over the aforementioned ROM) associated with the 38 mm, 42 mm, and 46 mm Equinoxe reverse shoulder was measured to be 0.371 in, 0.458 in, and 0.522 in, respectively.

Figure 57:
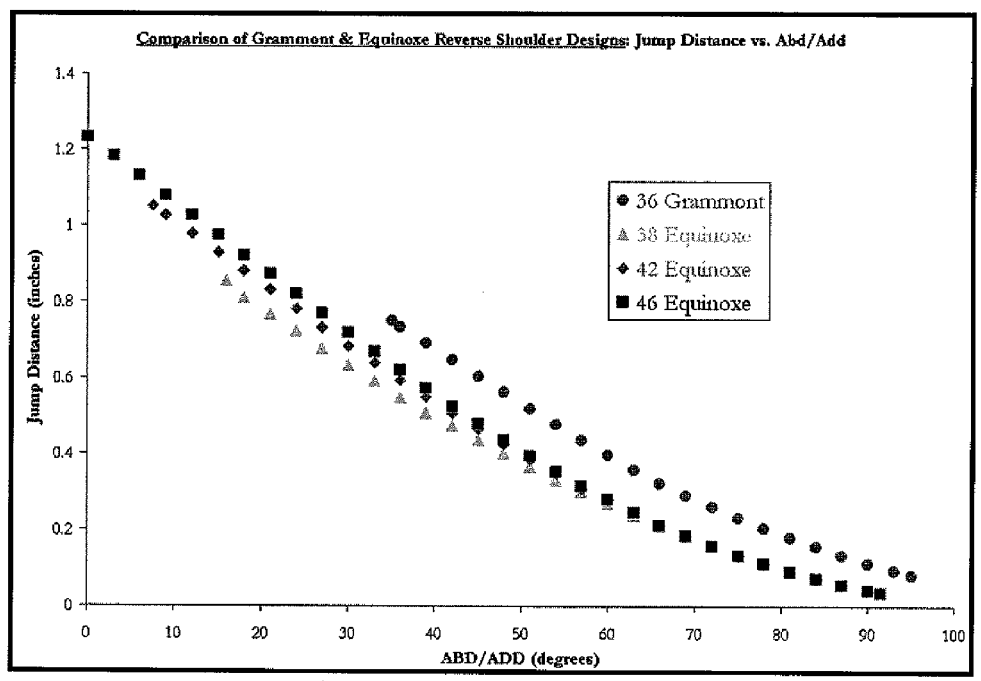
FIG. 57 shows a graph associated with a comparison of Jump Distance vs. Abduction/Adduction for an embodiment of the present invention and a typical Grammont Reverse Shoulder Prosthesis.

By comparison, the typical 36 mm Grammont reverse shoulder inferiorly and superiorly impinged at 35° and 95°, providing a total ROM of 60°. The minimum and maximum jump distance for this ROM was measured to be 0.081-0.749 inches; having an average jump distance of 0.374 in over this ROM (in 3° increments). As depicted in FIGS. 57 and 58, the Equinoxe reverse shoulder of this example is associated with a 20.5%, 28.6%, and 34.4% greater ROM and a −0.8%, a 18.3%, 28.3% greater average jump distance than the typical Grammont reverse shoulder prosthesis.

The results of this design verification demonstrate that the Equinoxe reverse shoulder prosthesis of this example is associated with more motion, less impingement, and a similar amount of stability as the typical 36 mm Grammont design.

Regarding this conclusion, three points should be considered. First, the ROM values obtained in this study are less than those reported clinically. The reason for this discrepancy is due at least in part to scapular motion not being considered in the analysis, only humeral motion was considered. The ratio of scapular motion to humeral motion has been reported between 0.4-0.7; depending upon the condition of the rotator cuff: the larger the cuff tear the greater the amount of scapular motion relative to humeral motion (see, De Wilde, L. F. et al. Functional Recovery after a Reverse Prosthesis for Reconstruction of the Proximal Humerus in Tumor Surgery. CORR. #430: 156-162. 2005; Mell, A. G. et al. Effect of Rotator Cuff Tear Size on Shoulder Kinematics. Transactions of the 51st Annual Meeting of the Orthopaedic Research Society. Poster #0623. 2005). Therefore, for cuff tear arthropathy, the most common indication for reverse shoulder arthroplasty, it is reasonable to assume that the amount of scapular motion relative to humeral motion is on the high end of this ratio—when this is considered, the results of this study comply with the clinical ROM data published in the literature.

Second, the average jump distance for the 38 mm Equinoxe reverse shoulder design of this example was 0.371 inches; this value is 0.003 inches (i.e. 0.075 mm) less than that of the typical 36 mm Grammont (0.374 inches). However, it is believed that this minute difference falls within the allowable manufacturing tolerances of either part and is also probably negligible when the accuracy and precision of the test methodology is considered. For this reason, it was concluded that these two designs have similar jump distances and therefore similar levels of stability.

Third, only the typical 36 mm Grammont design was considered, both Depuy and Tornier provide a 42 mm glenosphere. However, it is believed that the 42 mm prosthesis is rarely used clinically because the Grammont surgical technique typically requires reaming of the proximal humerus and 90%-95% of the time the proximal humerus is too small to accept a 42 mm humeral liner. Dr. Walch presented that the 42 mm glenosphere is used in <5% of his reverse arthroplasty cases at the 2005 American and Shoulder Elbow Society meeting in Orlando. Depuy in its Delta III marketing literature reported that the 42 mm glenosphere was used in only 11% of cases in 2004. Because the Equinoxe reverse shoulder of this example does not require reaming of the proximal humerus, (e.g. it is implanted using a traditional humeral head osteotomy along the anatomic neck of the humerus) it is possible to implant a larger diameter glenosphere. In this way, the size of the glenosphere used is determined based upon the size of glenoid, rather than the size of the proximal humerus. That being said, FIG. 58 approximated the ROM that would be associated with the 42 mm glenosphere design assuming the 42 mm humeral liner constraint was the same as that of the 36 mm humeral liner constraint. If this assumption is valid, then the same percentage increases in ROM of the Equinoxe reverse shoulder of this example over the typical 36 mm Grammont design would also apply for the typical 42 mm Grammont design.

For all these reasons, the results of this study have demonstrated that the Equinoxe reverse shoulder prosthesis of this example is associated with more motion, less impingement, and a similar amount of stability as the typical 36 mm Grammont design.

While a number of embodiments of the present invention have been described, it is understood that these embodiments are illustrative only, and not restrictive, and that many modifications may become apparent to those of ordinary skill in the art. For example, any element described herein may be provided in any desired size (e.g., any element described herein may be provided in any desired custom size or any element described herein may be provided in any desired size selected from a "family" of sizes, such as small, medium, large). Further, one or more of the components may be made from any of the following materials: (a) any biocompatible material (which biocompatible material may be treated to permit surface bone ingrowth or prohibit surface bone ingrowth—depending upon the desire of the surgeon); (b) a plastic; (c) a fiber; (d) a polymer; (e) a metal (a pure metal such as titanium and/or an alloy such as Ti—Al—Nb, Ti-6Al-4V, stainless steel); (f) any combination thereof. Further still, the metal construct may be a machined metal construct. Further still, various cage designs (e.g. square/elliptical/angled cages) may be utilized. Further still, various keel designs (e.g. anterior/posterior keel, medial/lateral keel, dorsal fin keel, angled keel) may be utilized. Further still, the prosthesis may utilize one or more modular elements. Further still, any desired number of cages(s) and/or keel(s) may be utilized with a given prosthesis. Further still, any number of protrusions (e.g., such as for initial fixation by forming a bond with cement and/or such as for supplemental fixation by forming a bond with cement) may be utilized with a given prosthesis. Further still, any number of female features that increase the cement mantle may be utilized with a given prosthesis. Further still, any number of male features that could dig into the bone so that initial/supplemental fixation can be improved may be utilized with a given prosthesis. Further still, any number of bone screws (e.g., such as for initial fixation and/or such as for supplemental fixation) may be utilized with a given prosthesis. Further still, any steps described herein may be carried out in any desired order (and any additional steps may be added as desired and/or any steps may be deleted as desired).

What is claimed is:

1. A glenoid assembly for a reverse shoulder prosthesis comprising:
   a glenosphere including a hollowed out portion, an articular surface,
      wherein the glenosphere has a central horizontal axis and a central vertical axis that intersect at a central point; and
   a glenoid plate including a body portion and a stem portion,
      wherein the glenoid plate is operatively connected to the hollowed out portion of the glenosphere,
      wherein the body portion of the glenoid plate has a front face, a back face and a thickness therebetween,
      wherein the body portion of the glenoid plate has a central horizontal axis that is shorter than a central vertical axis,
      wherein the central horizontal axis and the central vertical axis intersect at a central point that divides the body portion into an upper half, a lower half, a right half and a left half,
      wherein the stem portion has a central longitudinal axis which is 90 degrees relative to the central vertical axis of the body portion, and
      wherein the stem portion extends from the back face of the body portion of the glenoid plate from a position on the body portion of the glenoid plate such that the central longitudinal axis of the stem portion is superiorly shifted from the central point of the body portion of the glenoid plate along the central vertical axis,
      wherein the central point of the glenosphere and the central point of the body portion of the glenoid plate are aligned about a common horizontal axis.

2. The assembly of claim 1 wherein the front face of the body portion of the glenoid plate is a non-articulating surface.

3. The assembly of claim 1 wherein the stem portion has a cross-sectional shape selected from the group consisting of: cylindrical, square, rectangular and elliptical.

4. The assembly of claim 1 wherein the stem portion is hollow.

5. The assembly of claim 1 wherein the stem portion has a proximal end and a distal end, wherein the proximal end of the stem portion is attached to the back face of the body portion, and wherein at least one of the proximal end and the distal end has an opening.

6. The assembly of claim 5 wherein the opening provides access into an interior of the stem portion for placement of at least one of: (a) a therapeutic agent; and (b) a non-therapeutic agent.

7. The assembly of claim 6 wherein the therapeutic agent is selected from the group consisting of: (a) at least one supplemental graft material; (b) at least one antibiotic; and (c) at least one growth factor.

8. The assembly of claim 6 wherein the non-therapeutic agent comprises cement.

9. The assembly of claim 1 wherein the stem portion has a plurality of holes around a perimeter thereof.

10. The assembly of claim 9 wherein the plurality of holes around the perimeter of the stem portion provide access into an interior of the stem portion for bone growth from a glenoid into the stem portion.

11. The assembly of claim 1 wherein the stem portion extends from the back face of the body portion from a position on the body portion such that the central longitudinal axis of the stem portion is about 4 mm superiorly shifted from the central point of the body portion along the central vertical axis.

12. The assembly of claim 1 wherein the stem portion extends perpendicular from the back face of the body portion.

13. The assembly of claim 1 wherein the glenoid plate is operatively connected to the hollowed out portion of the glenosphere by the front face of the body portion and at least some of the thickness of the body portion.

14. The assembly of claim 13 wherein the hollowed out portion of the glenosphere in which at least some of the thickness of the body portion is disposed has a perimeter shape that is generally elongated along a superior-inferior axis.

15. The assembly of claim 13 wherein the hollowed out portion of the glenosphere in which at least some of the thickness of the body portion is disposed has a perimeter shape that is generally elongated along a superior-inferior axis to substantially match a perimeter shape of the glenoid plate.

16. The assembly of claim 13 wherein the hollowed out portion of the glenosphere in which at least some of the thickness of the body portion is disposed has a perimeter shape that is generally circular.

17. The assembly of claim 13 wherein the hollowed out portion of the glenosphere in which at least some of the thickness of the body portion is disposed has a perimeter shape that is generally circular to substantially match a perimeter shape of the glenoid plate.

18. The assembly of claim 1 wherein the glenoid plate is adapted to be attached to a glenoid.

19. The assembly of claim 1 wherein the glenoid plate is adapted to be attached to a glenoid having a central horizontal axis and a central vertical axis that intersect at a central point by the stem portion which is positioned in a hole at the central point.

20. The assembly of claim 19 wherein a distal rim of the glenoid plate is aligned with a distal edge of the glenoid.

* * * * *